US012746084B2

(12) United States Patent
Johnson et al.

(10) Patent No.: US 12,746,084 B2
(45) **Date of Patent: *Sep. 29, 2026**

(54) ROBOTIC SURGICAL SYSTEM AND METHOD FOR PROVIDING A STADIUM VIEW WITH ARM SET-UP GUIDANCE

(71) Applicant: Verb Surgical Inc., Santa Clara, CA (US)

(72) Inventors: Eric Johnson, Santa Clara, CA (US); Francois Brahic, Santa Clara, CA (US)

(73) Assignee: Auris Health, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/057,068

(22) Filed: Feb. 19, 2025

(65) Prior Publication Data

US 2025/0205003 A1 Jun. 26, 2025

Related U.S. Application Data

(63) Continuation of application No. 16/793,886, filed on Feb. 18, 2020, now Pat. No. 12,251,185.

(51) Int. Cl.
*A61B 34/37* (2016.01)
*A61B 34/00* (2016.01)
(Continued)

(52) U.S. Cl.
CPC .............. *A61B 34/37* (2016.02); *A61B 34/20* (2016.02); *A61B 34/25* (2016.02); *A61B 34/70* (2016.02);
(Continued)

(58) Field of Classification Search
CPC .. A61B 2017/00119; A61B 2034/2055; A61B 2034/2059; A61B 2034/252;
(Continued)

(56) References Cited

U.S. PATENT DOCUMENTS

2009/0192524 A1 7/2009 Itkowitz et al.
2010/0082039 A1 4/2010 Mohr et al.
(Continued)

FOREIGN PATENT DOCUMENTS

CN 105748026 A 7/2016
CN 106456266 A 2/2017
(Continued)

OTHER PUBLICATIONS

Decision of Patent Grant for Korean Application No. 10-2022-7032173 mailed May 12, 2025, with English translation.
(Continued)

*Primary Examiner* — Christopher L Cook
(74) *Attorney, Agent, or Firm* — Lempia Summerfield Katz LLC

(57) ABSTRACT

A robotic surgical system and method for providing a stadium view with arm set-up guidance is provided. In one embodiment, a robotic surgical system comprises a plurality of robotic arms, a display device, and a processor. The processor is configured to render, on the display device, a graphical representation of the plurality of robotic arms in their current positions, as well as user-guidance information on how to move the plurality of robotic arms to a different position. Other embodiments are provided.

18 Claims, 21 Drawing Sheets

(51) Int. Cl.
*A61B 34/20* (2016.01)
*A61B 34/30* (2016.01)

(52) U.S. Cl.
CPC . *A61B 2034/2059* (2016.02); *A61B 2034/305* (2016.02)

(58) Field of Classification Search
CPC ........ A61B 2034/254; A61B 2034/256; A61B 2034/305; A61B 34/20; A61B 34/25; A61B 34/37; A61B 34/70
See application file for complete search history.

(56) References Cited

U.S. PATENT DOCUMENTS

| | | | |
|---|---|---|---|
| 2013/0103197 | A1 | 4/2013 | Mohr |
| 2016/0314712 | A1 | 10/2016 | Grubbs |
| 2017/0172673 | A1 | 6/2017 | Yu et al. |
| 2017/0172674 | A1 | 6/2017 | Hanuschik |
| 2017/0239000 | A1 | 8/2017 | Moctezuma De La Barrera et al. |
| 2019/0183591 | A1 | 6/2019 | Johnson |
| 2020/0253678 | A1 | 8/2020 | Hulford et al. |
| 2020/0337789 | A1 | 10/2020 | Meglan |
| 2021/0228282 | A1 | 7/2021 | Dimaio et al. |
| 2022/0022982 | A1 | 1/2022 | Hares et al. |

FOREIGN PATENT DOCUMENTS

| | | | |
|---|---|---|---|
| CN | 109069136 | A | 12/2018 |
| WO | 2016187054 | A1 | 11/2016 |
| WO | 2019023378 | A1 | 1/2019 |
| WO | 2019139935 | A1 | 7/2019 |
| WO | 2019177711 | A1 | 9/2019 |

OTHER PUBLICATIONS

European Search Report for European App. No. 20920289.4 mailed Feb. 20, 2024.

Farah, Edris, and Liu Shaogang. "Kinematics Modeling and Simulating of a New Surgical Robot." International Journal of Control and Automation 8.8 (2015): 363-372.

ROBOTIC SURGICAL SYSTEM AND METHOD FOR PROVIDING A STADIUM VIEW WITH ARM SET-UP GUIDANCE

RELATED APPLICATION

This application is a continuation of U.S. application Ser. No. 16/793,886, filed Feb. 18, 2020, which is hereby incorporated by reference in its entirety.

TECHNICAL FIELD

The following embodiments generally relate to the field of robotic surgery and more specifically to a graphical user interface (GUI) for a robotic surgical system that provides a stadium view with arm set-up guidance.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more surgical instruments (e.g., an end effector, at least one camera, etc.) through the incisions into the patient. The surgical procedures may then be performed using the introduced surgical instruments, with the visualization aid provided by the camera.

Generally, MIS provides multiple benefits, such as reduced patient scarring, less patient pain, shorter patient recovery periods, and lower medical treatment costs associated with patient recovery. In some embodiments, MIS may be performed with robotic systems that include one or more robotic arms for manipulating surgical instruments based on commands from an operator. A robotic arm may, for example, support at its distal end various devices, such as surgical end effectors, imaging devices, cannulae for providing access to the patient's body cavity and organs, etc.

In some embodiments, the operator may provide commands for manipulating surgical instruments while viewing an image that is provided by a camera and displayed on a display to the user.

DETAILED DESCRIPTION

Non-limiting examples of various aspects and variations of the embodiments are described herein and illustrated in the accompanying drawings.

Robotic Surgical System Overview

Figure 1A:
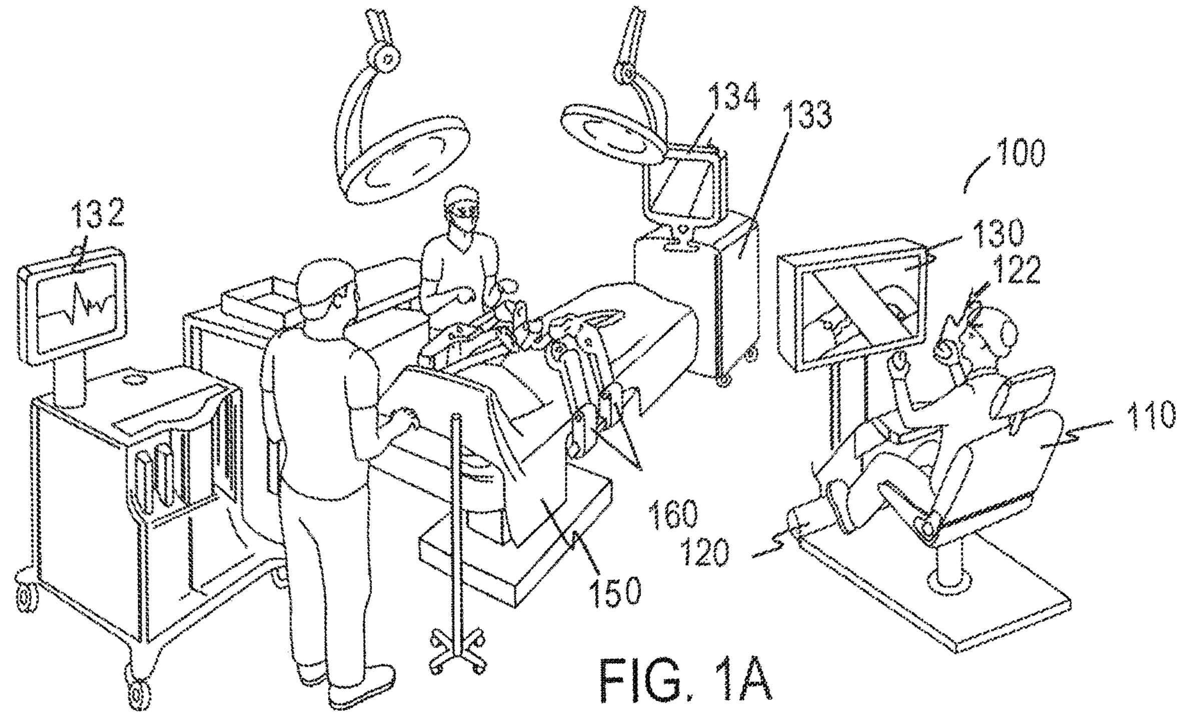
FIG. 1A depicts an example of an operating room arrangement with a robotic surgical system and a user console of an embodiment.

FIG. 1A is an illustration of an exemplary operating room environment with a robotic surgical system. Generally, as shown in FIG. 1A, the robotic surgical system includes a user console 100 (sometimes referred to herein as the "surgeon bridge" or "bridge"), a control tower 133, and one or more robotic arms 160 located at a robotic platform (e.g., table, bed, etc.), where surgical instruments (e.g., with end effectors) are attached to the distal ends of the robotic arms 160 for executing a surgical procedure. The robotic arms 160 are shown as a table-mounted system, but in other configurations, one or more robotic arms may be mounted to a cart, ceiling or sidewall, or other suitable support surface.

Figure 1B:
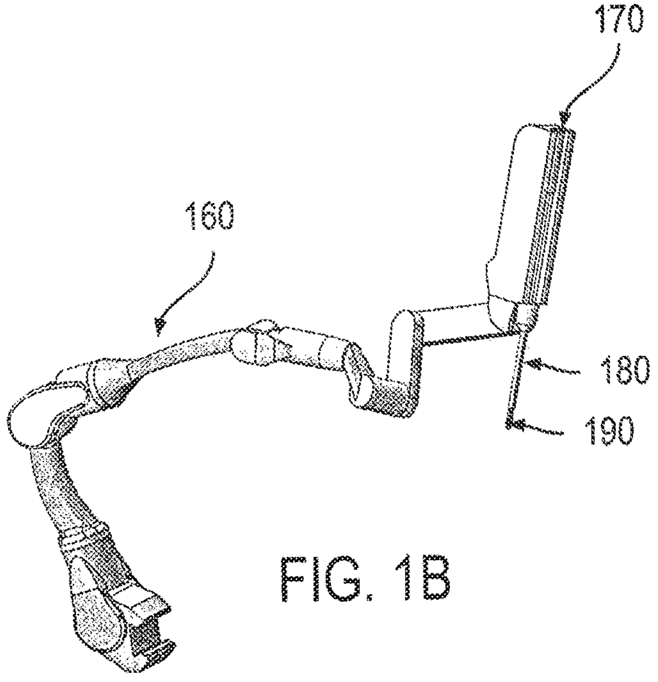
FIG. 1B is a schematic illustration of one exemplary variation of a robotic arm manipulator, tool driver, and cannula with a surgical tool of an embodiment.

As further illustration, as shown in the exemplary schematic of FIG. 1B, a robotic surgical system may include at least one robotic arm 160 and a tool driver 170 generally attached to a distal end of the robotic arm 160. A cannula 180 coupled to the end of the tool driver 170 may receive and guide a surgical instrument 190 (e.g., end effector, camera, etc.). Furthermore, the robotic arm 160 may include a plurality of links that are actuated so as to position and orient the tool driver 170, which actuates the surgical instrument 190.

Generally, as shown in FIG. 1A, the user console 100 may be used to interface with the robotic surgical system 150. A user (such as a surgeon or other operator) may use the user console 100 to remotely manipulate the robotic arms 160 and/or surgical instruments (e.g., in tele-operation). The user console 100 may be located in the same operating room as the robotic system 150, as shown in FIG. 1A. In other embodiments, the user console 100 may be located in an adjacent or nearby room, or tele-operated from a remote location in a different building, city, or country. In one example, the user console 100 may comprise a seat 110, foot-operated controls (pedals) 120, one or more handheld user input devices 122, and at least one user display 130 configured to display, for example, a view of the surgical site inside a patient (e.g., captured with an endoscopic camera), and/or other surgical or medical information.

Figure 1C:
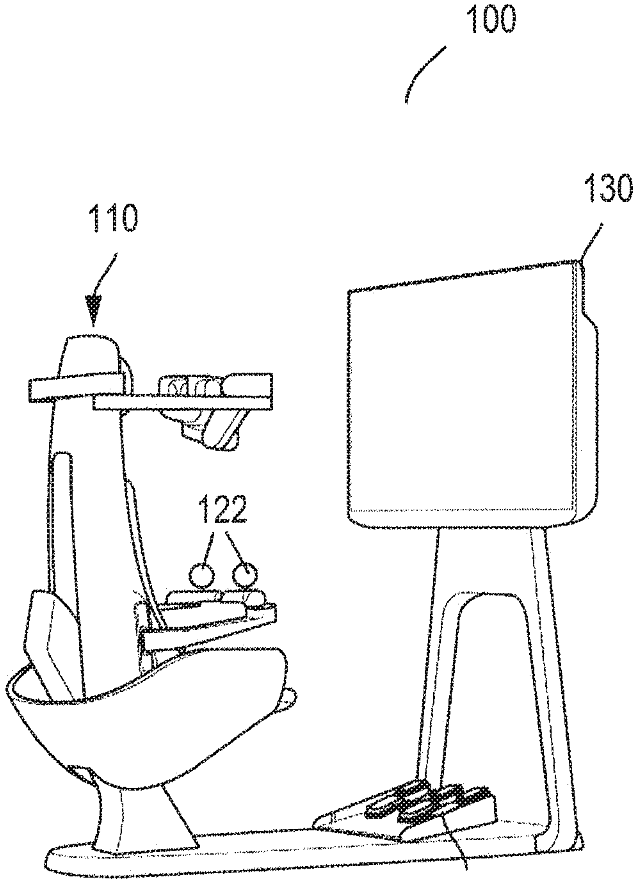
FIG. 1C is a schematic illustration of an exemplary user console of an embodiment.

In the exemplary user console shown in FIG. 1C, a user located in the seat 110 and viewing the user display 130 may manipulate the foot-operated controls 120 and/or handheld user input devices 122 to remotely control the robotic arms 160 and/or surgical instruments mounted to the distal ends of the arm. The foot-operated controls 120 and/or handheld user input devices 122 may additionally or alternatively be used to control other aspects of the user console 100 or robotic system 150. For example, in variations in which the user generally controls (at any given time) a designated "left-hand" robotic arm/instrument and a designated "right-hand" robotic arm/instrument, the foot-operated controls 120 may enable a user to designate from among a larger group of available robotic arms/instruments which robotic arms/instruments comprise the "left-hand" and "right-hand" robotic arm/instruments (e.g., via toggle or rotation in selection among the available robotic arms/instruments). Other examples include adjusting or configuring the seat 110, the foot-operated controls 120, the user input devices 122, and/or the user display 130.

In some variations, a user may operate the surgical robotic system in an "over the bed" (OTB) mode, in which the user is at the patient's side and simultaneously manipulating a robotically-driven instrument/end effector attached thereto (e.g., with a handheld user input device 122 held in one hand) and a manual laparoscopic tool. For example, the user's left hand may be manipulating a handheld user input device 122 to control a robotic surgical component, while the user's right hand may be manipulating a manual laparoscopic tool. Accordingly, in these variations, the user may perform both robotic-assisted MIS and manual laparoscopic surgery on a patient.

During an exemplary procedure or surgery, the patient is prepped and draped in a sterile fashion, and anesthesia may be achieved. Initial access to the surgical site may be performed manually with the robotic system 150 in a stowed configuration or withdrawn configuration to facilitate access to the surgical site. Once access is completed, initial positioning and/or preparation of the robotic system may be performed. During the surgical procedure, a surgeon or other user in the user console 100 may utilize the foot-operated controls 120, user input devices 122, and/or other suitable controls to manipulate various end effectors and/or imaging systems to perform the procedure. Manual assistance may be provided at the procedure table by other personnel, who may perform tasks including but not limited to retracting tissues, or performing manual repositioning or tool exchange involving one or more robotic arms 160. Other personnel may be present to assist the user at the user console 100. Medical and surgery-related information to aid other medical personnel (e.g., nurses) may be provided on additional displays such as a display 134 on a control tower 133 (e.g., control system for the robotic surgical system) and/or a display 132 located bedside proximate the patient. For example, as described in further detail herein, some or all information displayed to the user in the user console 100 may also be displayed on at least one additional display for other personnel and/or provide additional pathways for inter-personnel communication. When the procedure or surgery is completed, the robotic system 150 and/or user console 100 may be configured or set in a state to facilitate one or more post-operative procedures, including but not limited to robotic system cleaning and/or sterilization, and/or healthcare record entry or printout, whether electronic or hard copy, such as via the user console 100.

In some variations, the communication between the robotic system 150, the user console 100, and any other displays may be through the control tower 133, which may translate user commands from the user console 100 to robotic control commands and transmit them to the robotic system 150. The control tower 133 may transmit status and feedback from the robotic system 150 back to the user console 100 (and/or other displays). The connections between the robotic system 150, the user console 100, other displays, and the control tower 133 may be via wired and/or wireless connections, and may be proprietary or performed using any of a variety of data communication protocols. Any wired connections may be built into the floor and/or walls or ceiling of the operating room. The robotic surgical system may provide video output to one or more displays, including displays within the operating room as well as remote displays accessible via the Internet or other networks. The video output or feed may be encrypted to ensure privacy, and all or one or more portions of the video output may be saved to a server, an electronic healthcare record system, or other suitable storage medium.

In some variations, additional user consoles 100 may be provided, for example to control additional surgical instruments, and/or to take control of one or more surgical instruments at a primary user console. This will permit, for example, a surgeon to take over or illustrate a technique during a surgical procedure with medical students and physicians-in-training, or to assist during complex surgeries requiring multiple surgeons acting simultaneously or in a coordinated manner.

Figure 2:
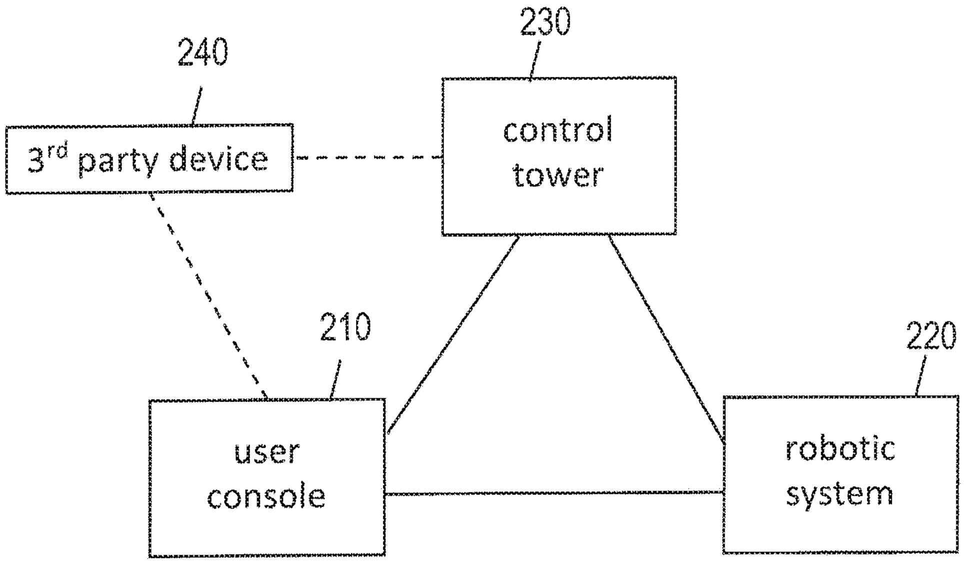
FIG. 2 is a schematic illustration of an exemplary variation of a user console for a robotic surgical system of an embodiment in communication with one or more third party devices.

In some variations, as shown in the schematic illustration of FIG. 2, one or more third party devices 240 may be configured to communicate with the user console 210 and/or other suitable portions of the robotic surgical system. For example, as described elsewhere herein, a surgeon or other user may sit in the user console 210, which may communicate with the control tower 230 and/or robotic instruments in a robotic system 220. Medical data (e.g., endoscopic images, patient vitals, tool status, etc.) may be displayed at the user console 210, the control tower 230, and/or other displays. At least a subset of the surgical and other medical-related information may furthermore be displayed at a third party device 240, such as a remote computer display that is viewed by a surgical collaborator in the same room or outside the room. Other communication, such as teleconferencing with audio and/or visual communication, may further be provided to and from the third party device. The surgical collaborator may be, for example, a supervisor or trainer, a medical colleague (e.g., radiologist), or other third party who may, for example, view and communicate via the third party device 240 to assist with the surgical procedure.

Figure 3:
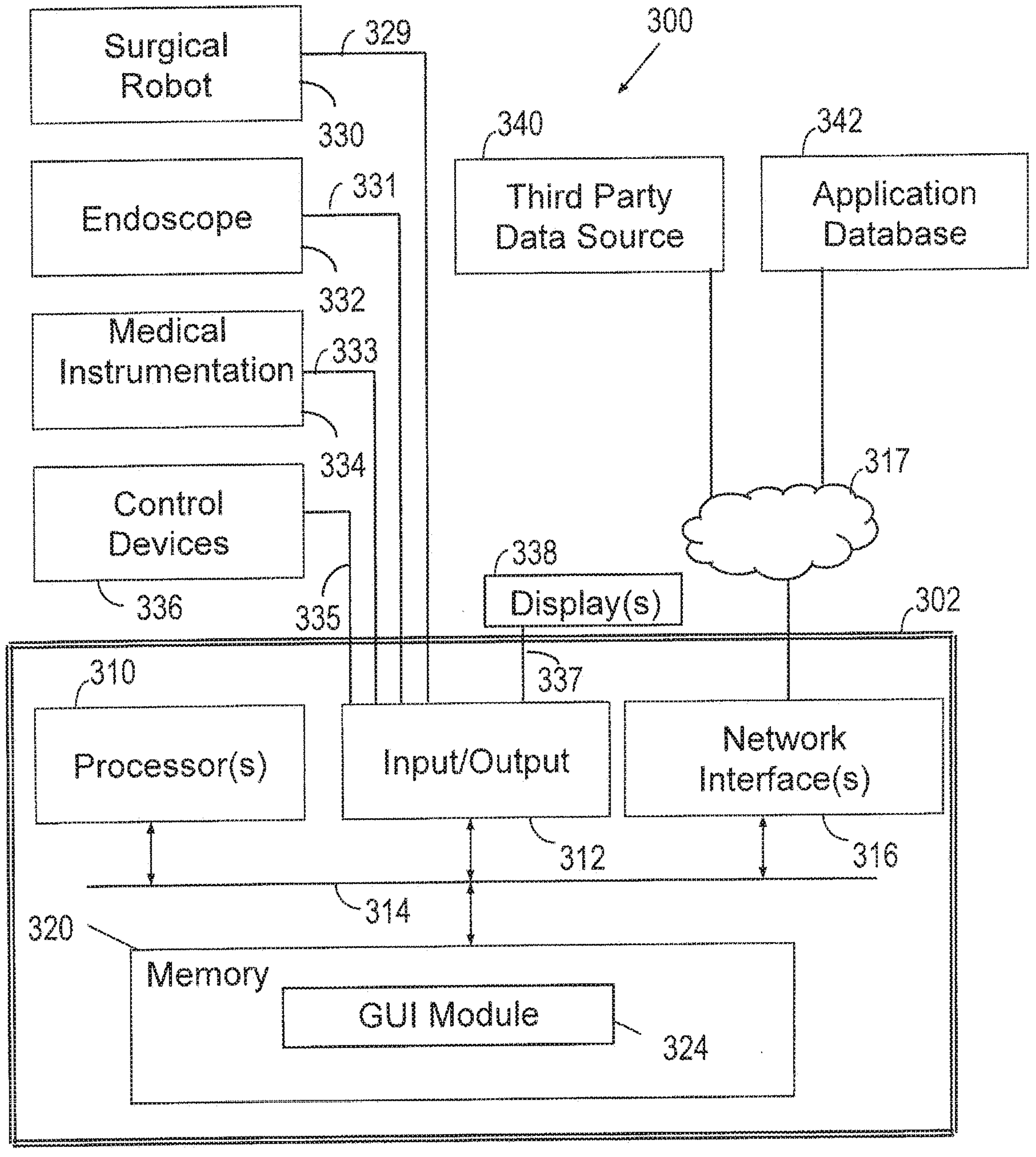
FIG. 3 is a schematic of a surgical robotic platform of an embodiment with a graphical user interface (GUI) module, where the surgical robotic platform is in communication with multiple medical data resources.

FIG. 3 is a schematic illustration of an exemplary variation of a system 300 including a robotic surgical system and its interaction with other devices and parties. Although a particular architecture of the various connected and communicating systems is depicted in FIG. 3, it should be understood that in other variations, other suitable architectures may be used and the arrangement shown in FIG. 3 is for illustrative purposes. The system 300 may include a surgical robotic platform 302 that facilitates the integration of medical data from discrete medical data resources generated from a variety of parties. Data from the discrete medical data resources may, for example, be used to form temporally coordinated medical data. Multi-panel displays of the temporally coordinated medical data may be configured and presented, as described further herein.

The platform 302 may be, for example, a machine with one or more processors 310 connected to one or more input/output devices 312 via a bus 314. The at least one processor may, for example, include a central processing unit, a graphics processing unit, an application specific integrated circuit, a field programmable logic device or combinations thereof.

The surgical robotic platform 302 may include one or more input ports to receive medical data from discrete medical data resources. For example, a surgical robot port 329 may receive surgical robot data from a surgical robot 330. Such data may, for example, include position data or other suitable status information. An imaging port 331 may receive imaging data from an imaging device 332, such as an endoscope, that is configured to capture images (e.g., still images, video images) of a surgical site. The endoscope may, for example, be inserted through a natural orifice or through an aperture in a surgical patient. As another example, one or more medical instrumentation ports 333 may receive patient vital information from medical instrumentation 334 (e.g., a pulse oximeter, electrocardiogram device, ultrasound device and/or the like). Additionally, as another example, one or more user control data ports 335 may receive user interaction data from one or more control devices that receive user inputs from a user for controlling the system. For example, one or more handheld user input devices, one or more foot pedals, and/or other suitable devices (e.g., eye tracking, head tracking sensors) may receive user inputs.

The surgical robotic platform 302 may further include one or more output ports 337 configured for connection to one or more displays 338. For example, the displays 338 may include an open display (e.g., monitor screen) in a user console, an immersive display or head-mounted device with a display, on supplemental displays such as on a control tower display (e.g., team display), a bedside display (e.g., nurse display), an overhead "stadium"-style screen, etc. For example, the graphical user interface disclosed herein may be presented on one or more displays 338. The one or more displays 338 may present three-dimensional images. In some variations, the one or more displays 338 may include a touchscreen. The one or more displays 138 may be a single display with multiple panels, with each panel presenting different content. Alternatively, the one or more displays 138 may include a collection of individual displays, where each individual display presents at least one panel.

In some variations, a network interface 316 may also be connected to the bus 314. The network interface 316 may, for example, provide connectivity to a network 317, which may be any combination of one or more wired and/or wireless networks. The network 317 may, for example, help enable communication between the surgical robotic platform 302 and other data sources or other devices. For example, one or more third party data sources 340 may also be connected to the network 317. The third party source 340 may include a third party device (e.g., another computer operated by a third party such as another doctor or medical specialist), a repository of video surgical procedure data (e.g., which may be relevant to a procedure being performed by a surgeon), or other suitable source of additional information related to a surgical procedure. For example, the third party device data may be ported to a panel that is displayed to a surgeon before, during or after a procedure.

As another example, one or more application databases 342 may be connected to the network 317 (or alternatively, stored locally within a memory 320 within the surgical robotic platform 302). The application database 342 may include software applications (e.g., as described in further detail below) that may be of interest to a surgeon during a procedure. For example, a software application may provide access to stored medical records of a patient, provide a checklist of surgical tasks for a surgical procedure, perform machine vision techniques for assisting with a procedure, perform machine learning tasks to improve surgical tasks, etc. Any suitable number of applications may be invoked. Information associated with an application may be displayed in a multi-panel display or other suitable display during a procedure. Additionally or alternatively, information provided by one or more applications may be provided by separate resources (e.g., a machine learning resource) otherwise suitably in communication with the surgical robotic platform 302.

In some variations, one or more of the software applications may run as a separate process that uses an application program interface (API) to draw objects and/or images on the display. APIs of different complexities may be used. For example, a simple API may include a few templates with fixed widget sizes and locations, which can be used by the GUI module to customize text and/or images. As another example, a more complex API may allow a software application to create, place, and delete different widgets, such as labels, lists, buttons, and images.

Additionally or alternatively, one or more software applications may render themselves for display. This may, for example, allow for a high level of customization and complex behavior for an application. For example, this approach may be implemented by allowing an application to pass frames that are rendered by a graphical user interface (GUI) module 324, which can be computer-readable program code that is executed by the processor 310. Alternatively, an image buffer may be used as a repository to which an application renders itself.

In some variations, one or more software applications may run and render themselves independent of the GUI module 324. The GUI module may still, however, launch such applications, instruct the application or the operating system where the application is to be positioned on the display, etc.

As another approach, in some variations, one or more applications may run completely separate from the GUI rendered by the GUI module. For example, such applications may have a physical video connection and data connection to the system (e.g., through suitable input/output devices, network, etc.). The data connection may be used to configure video feed for an application to be the appropriate pixel dimensions (e.g., full screen, half screen, etc.).

As shown in FIG. 3, in some variations, a memory 320 may also be connected to the bus 314. The memory 320 may be configured to store data processed in accordance with embodiments of the methods and systems described herein.

In some variations, the memory 320 may be configured to store other kinds of data and/or software modules for execution. For example, a user console may include a memory 320 that stores a GUI module 324 with executable instructions to implement operations disclosed herein. The GUI module may, for example, combine and aggregate information from various software applications and/or other medical data resources for display. In some exemplary variations, one or more software applications may be incorporated into base code of the GUI module, such that the module draws graphics and displays text in the appropriate location on the display. For example, the module may fetch the images from a database, or the images may be pushed to the interface from an instrument (e.g., endoscopic camera) in the operating room, via a wired or wireless interface.

In some variations, medical data may be collected from discrete medical data resources (e.g., surgical robot 330, endoscope 332, medical instrumentation 334, control devices 336, third party data source 340, application database 342, etc.). Additionally, at least some of the medical data may be temporally coordinated such that, when necessary, time sensitive information from different medical data resources is aligned on a common time axis. For example, surgical robot position data may be time coordinated with endoscope data, which is coordinated with operator interaction data from control devices. Similarly, a networked resource, such as information provided by one or more software applications, may be presented at an appropriate point in time along with the other temporally coordinated data. Multi-panel displays, and/or other suitable displays, may be configured to communicate medical information (e.g., including the temporally coordinated medical data) as part of a graphical user interface (GUI).

In some embodiments, the GUI may be displayed in a multi-panel display at a user console that controls the robotic surgical system. Additionally or alternatively, the GUI may be displayed at one or more additional displays, such as at a control tower for the robotic surgical system, at a patient bedside, etc. Generally, the GUI may provide for more effective communication of information to a user in the user console and/or other personnel, as well as for more effective communication and collaboration among different parties involved in a surgical procedure.

The following section described one particular embodiment that can be used with the GUI of the robotic surgical system 150. Examples of other GUI embodiments are described in "Multi-Panel Graphical User Interface for a Robotic Surgical System," U.S. patent application Ser. No. 15/842,485, filed Dec. 14, 2017, which is hereby incorporated by reference.

Stadium View Application for a GUI

In one embodiment, the GUI runs a "stadium view" app that renders a graphical representation (i.e., not an actual camera view) of current positions of the table and the plurality of robotic arms 160. The stadium view can also show additional information, such as, but not limited to, graphical representations of the patient, the operating room staff, and/or other elements of the operating room environment. The graphical representations can be two-dimensional or three-dimensional and can be generated by the robotic surgical system 150 or rendered by a separate component and provided to the stadium app for display.

The current positions can be derived from real-time or near real-time information relating to a current position of the table and the plurality of robotic arms 160. For example, the graphical representation (sometimes referred to herein as a "rendering") of a robotic arm may be based at least in part on one or more kinematic algorithms that control the robotic arm. The one or more kinematic algorithms may be fed into a modeling module that transforms the kinematic information into a rendered two- or three-dimensional model. As another example, the rendering of the robotic arms and/or table may be based at least partially on one or more sensors (e.g., position sensors in a robotic arm, infrared sensors around the operating room tracking markers placed on the robotic arms 160 or table, etc.).

This stadium view can provide a user with an "outside-the-patient-body" view of the robotic surgical system 150, the patient, and/or staff, etc. in the operating room. The user may, for example, monitor status of the robotic system, such as tool status, potential collisions, etc. and communicate to other members of the surgical team about such status and resolution of any issue. Furthermore, in some variations, the user may interact with the graphical representation within the stadium view application and effect one or more changes in the robotic surgical system, as described below.

Figure 4A:
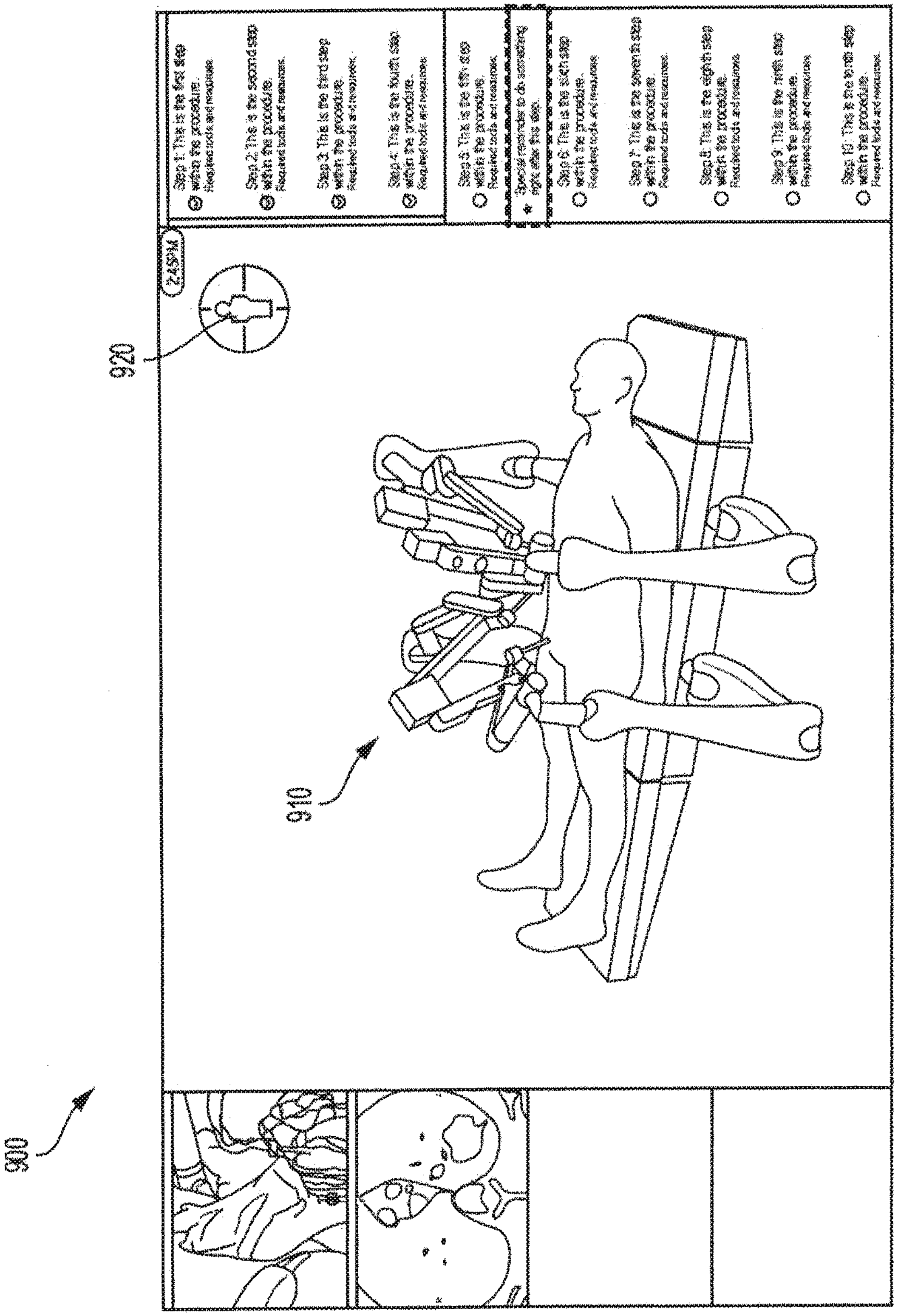
FIGS. 4A-4E are exemplary variations of a graphical user interface of an embodiment that includes a stadium view application.

An exemplary implementation of a stadium view application is shown in FIG. 4A. As shown in FIG. 4A, a stadium view application 900 may display a 3D rendering 910 of a patient on a patient table, and a plurality of robotic arms docked to the patient. A perspective guide 920 may additionally be displayed to indicate what view of the 3D rendering is currently being displayed (e.g., perspective view, plan view, etc.). Furthermore, as shown in, for example, FIG. 4C, at least some of the robotic arms may be numerically labeled, so as to distinguish between different robotic arms (e.g., help enable better communication regarding the status of a particular arm). In another view within a stadium view application 900, additional information regarding status of the robotic system (e.g., what kinds of tools are attached to respective robotic arms, activation state of tools, etc.) may additionally be displayed proximate a rendering 910.

Figure 4B:
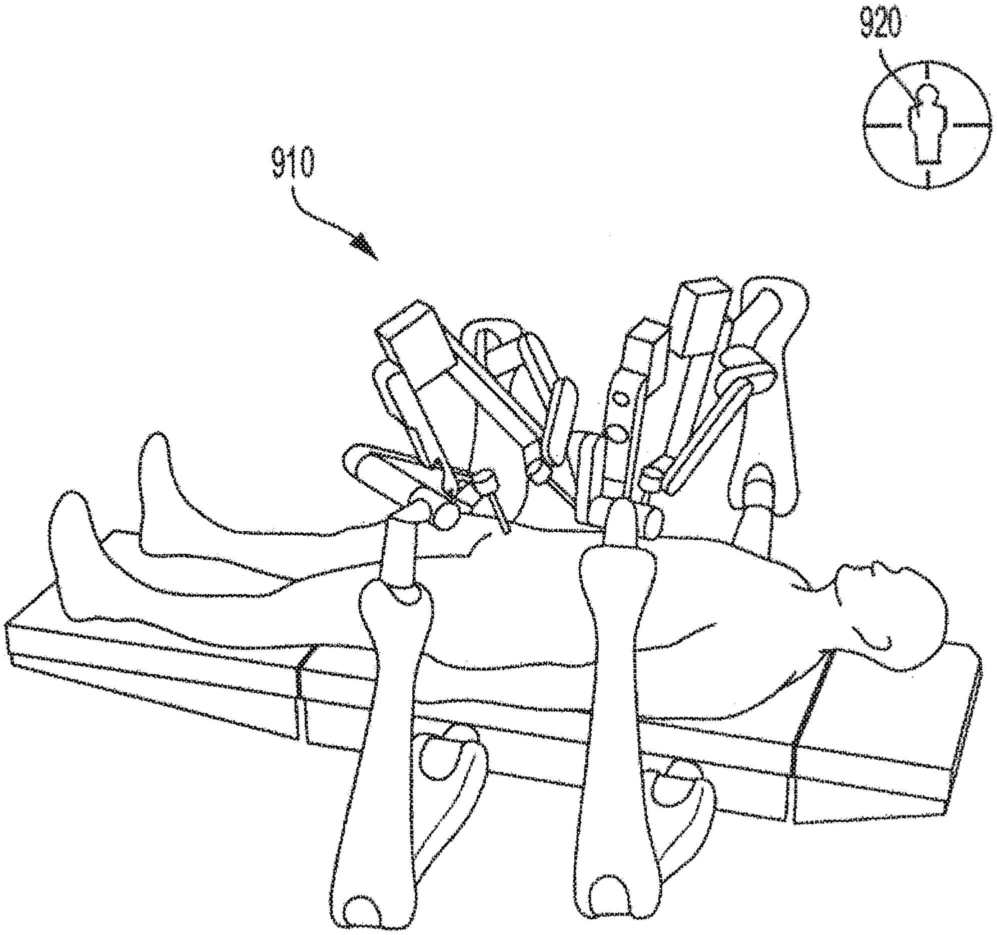
Figure 4C:
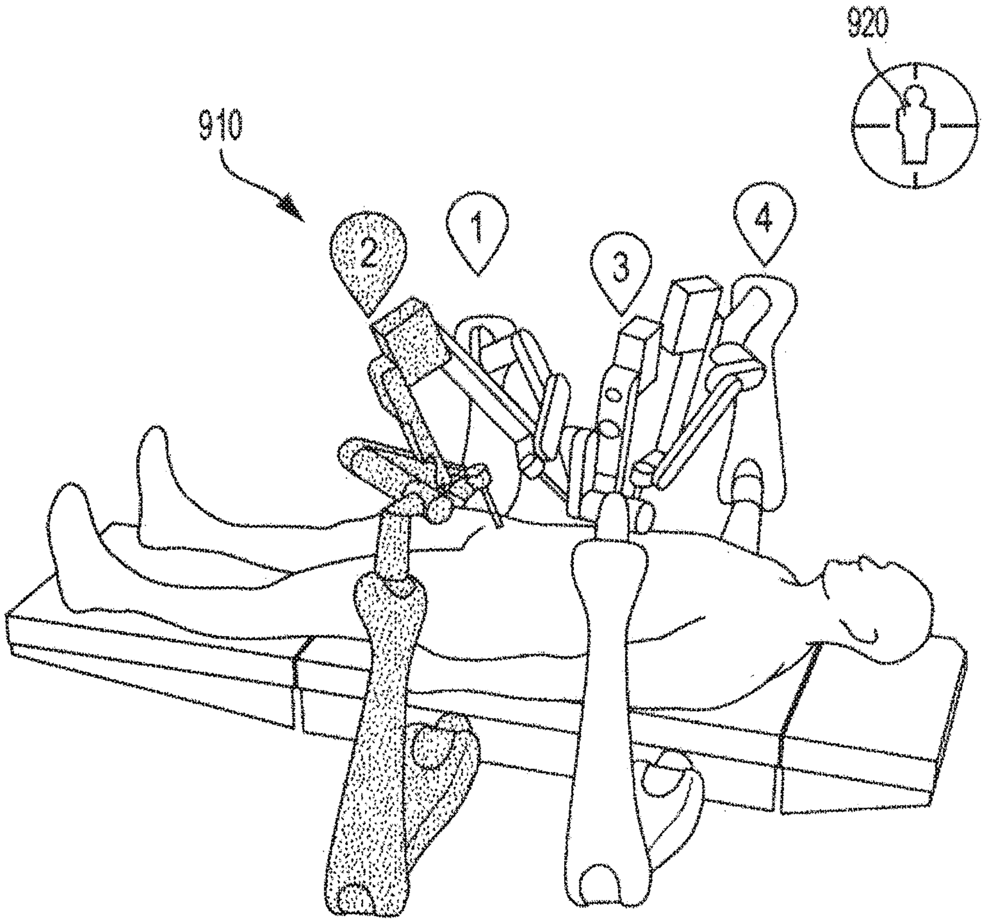

The display of the 3D rendering 910 in the stadium view application may be modified based on status of the rendered objects. For example, as shown in FIG. 4B, the rendering 910 is generally a nominal rendering, with no particular portions of the rendering 910 selected or highlighted. As shown in FIG. 4C, the stadium view application may be configured to highlight at least one of the robotic arms (labeled "2" in FIG. 4C), such as in response to a user selection of the arm. For example, a user may select a particular robotic arm and in response, the stadium view application may display information regarding status of the selected arm. As shown in, for example, FIG. 4E, in response to a user selection of an arm, the stadium view application may also display and/or highlight information relating to the selected arm and its associated tool, such as tool type (e.g., "scissors"), tool status (e.g., operation state such as "cut" or "coagulate", and/or staples remaining, etc.) and the like. As another example, a user may select a particular robotic arm such that it is highlighted in both the user's displayed GUI and in another displayed instance of the GUI (e.g., on a control tower display) to more easily communicate with other surgical staff regarding that robotic arm, thereby reducing confusion.

As another example, a user may select a robotic arm rendered in the stadium view application and move it (e.g., through a click-and-drag interaction) to effect a change in the position (pose) of the actual selected robotic arm. The movement of the selected rendered robotic arm may, for example, be communicated to a robotic arm controller that resolves the new position into a series of one or more actuator commands to actuated joints in the robotic arm such that the robotic arm position matches the new position of the rendered robotic arm. Accordingly, the stadium view application may provide a way to help enable a user in a user console "manually" reposition a robotic arm from the user console, without physically contacting the robotic arm. Similarly, the position of the patient table may be adjusted via adjustment of the rendered patient table within the stadium view app.

Figure 4D:
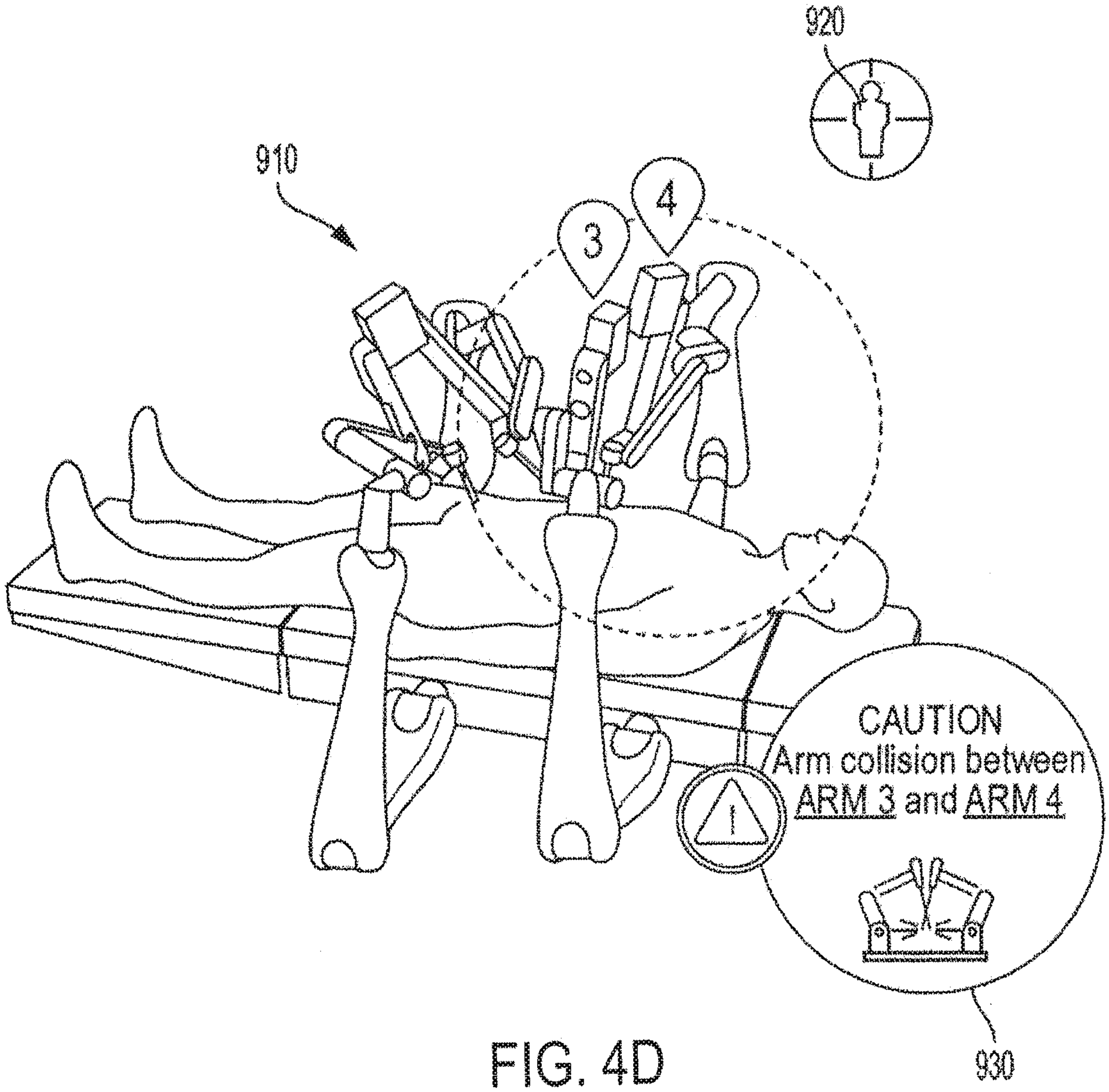
Figure 4E:
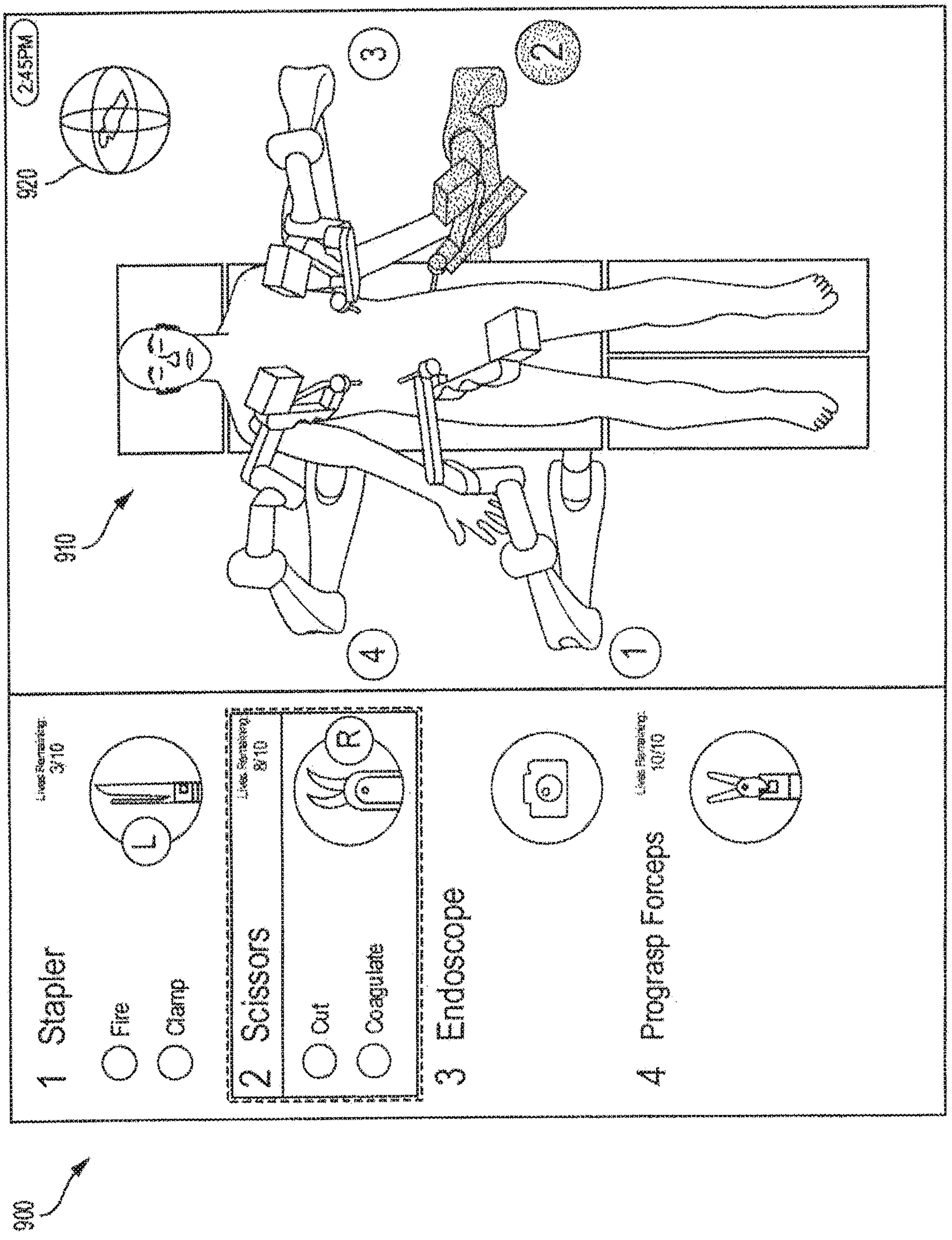

In some variations, the stadium view application may be configured to notify a user of a collision between robotic arms. In some variations, a collision (e.g., impending or occurred) may be detected based on proximity or contact sensors on robotic arms, machine vision techniques, and/or in any suitable manner. In response to receiving information indicating that a collision is impending or has occurred, the stadium view application may highlight one or more robotic arms involved in the collision. For example, as shown in FIG. 4D, one or more rendered robotic arms (labeled "3" and "4") may be highlighted. Additionally or alternatively, an alert notification 930 may be displayed explaining the collision. Audio alerts indicating a collision may additionally be provided to the user through the stadium view application. It should be understood that in other variations, the stadium view application may provide alerts or notifications for other kinds of status updates, such as surgical instrument errors, in a similar manner. For example, the rendered display of other portions of the robotic system, and/or other suitable portions of the operating room environment, may be highlighted to indicate other kinds of status changes or provide suitable updates. Notifications similar to alert notification 930 for other kinds of status updates may also be provided via the stadium view application.

In the above examples, the stadium view was used intraoperatively during surgery to provide the surgeon (using a display on the bridge 100) and/or staff (e.g., using the display 134 on the control tower 133 or the display 132 located bedside adjacent to/proximate the patient) with a real-time or near-real-time view of the position of the robotic arms 160 to warn of possible collisions between the arms 160 and/or other objects. The above examples also show that the stadium view can be used by the surgeon during surgery to guide the staff during instrument swaps on the robotic arms. As shown by these examples, because the stadium view provides a way for the surgeon to have a real- or near-real-time outside-of-the-body view of the robotic arms 160, table, and patient from the surgeon console 100, this embodiment allows the surgeon to have better communication with bedside staff during the surgery. That is, using stadium view, the surgeon, at the surgeon console 100, may have a better understanding of what is going on at the bedside and communicate clearly with bedside staff, as the surgeon would have a real-time (or near-real time) view of the arms 160 with identification of the arms 160 and tool names. The stadium view also can provide feedback, such as an error or warning information to help resolve issues (e.g., arm collisions).

In another example, the stadium view can be used pre-op and/or post-op to guide staff (e.g., nurses) through arm setup and/or teardown by providing user-guidance information on how to move the plurality of robotic arms 160 to a different position. Pre-op/post-op arm setup/teardown are non-trivial processes that users of the robotic surgical system 150 have to face. Users may find the visual guidance offered by the stadium view of this embodiment easier to follow and more desirable than text guidelines. For example, a particular robotic arm may be highlighted in the stadium view application during setup of the robotic system to indicate that the next tool according to a procedure template application should be attached to that particular robotic arm. Other guidance, such as text descriptions and/or other graphical representations of tools and animations (video), etc., may be provided via the stadium view app to further help surgical staff set up, teardown, or otherwise tend to the system. The following paragraphs and FIGS. 5-12 provide more information about this embodiment.

Figure 5:
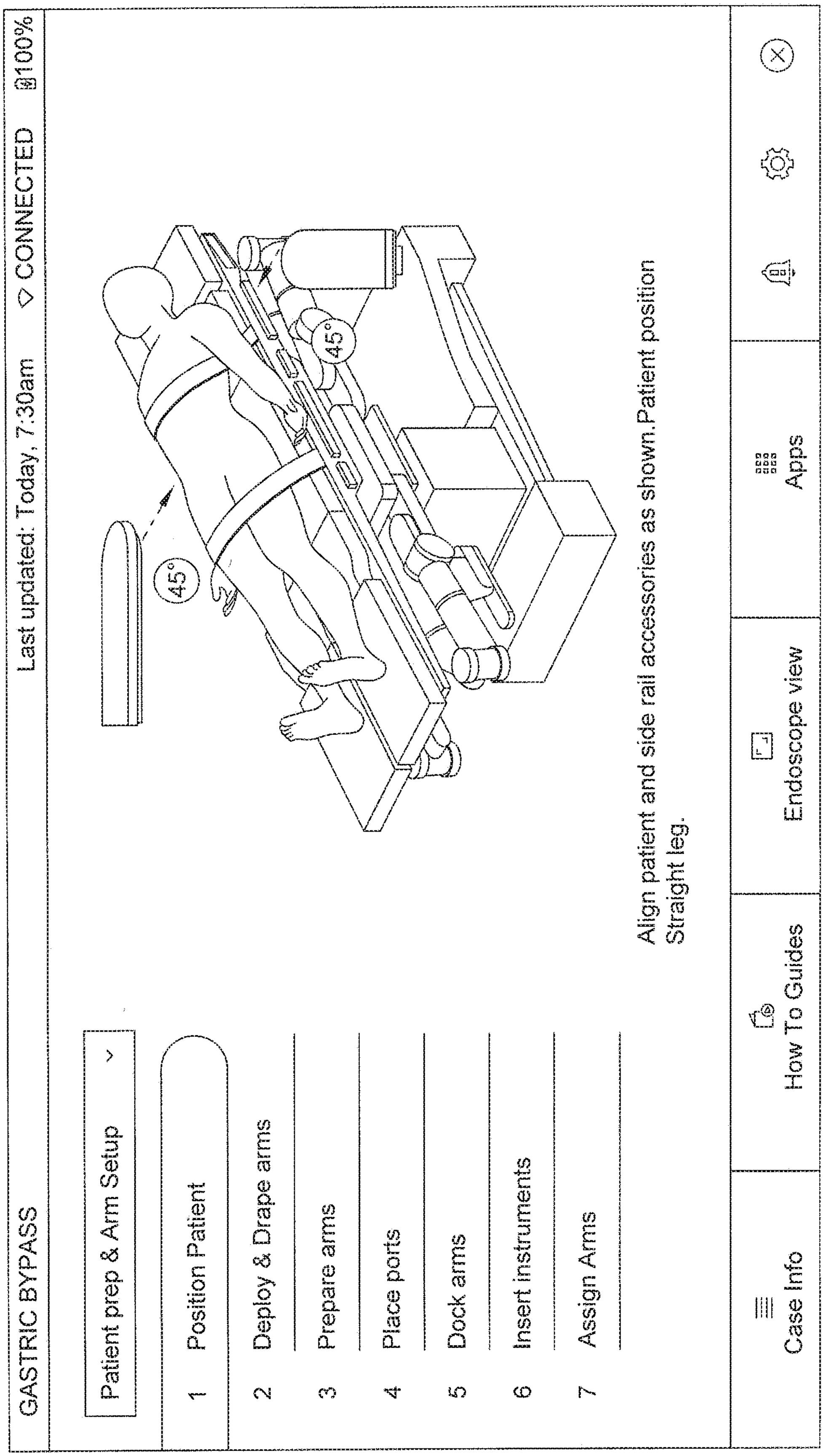
FIG. 5 is an illustration of a graphical user interface of an embodiment that includes a stadium view application that provides user-guidance information on how to position a patient.
Figure 6:
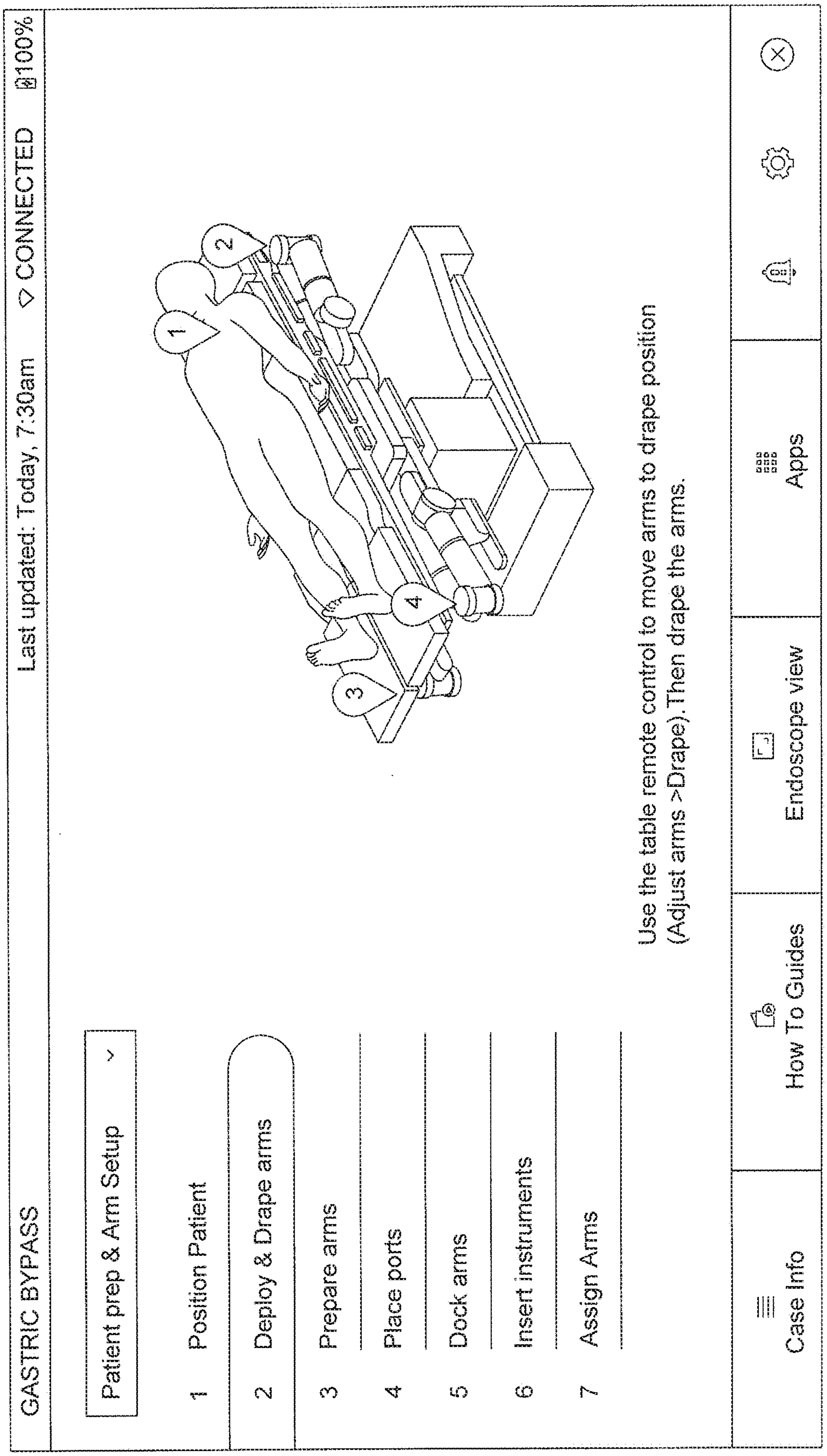
FIG. 6 is an illustration of a graphical user interface of an embodiment that includes a stadium view application that provides user-guidance information on how to deploy robotic arms.
Figure 7:
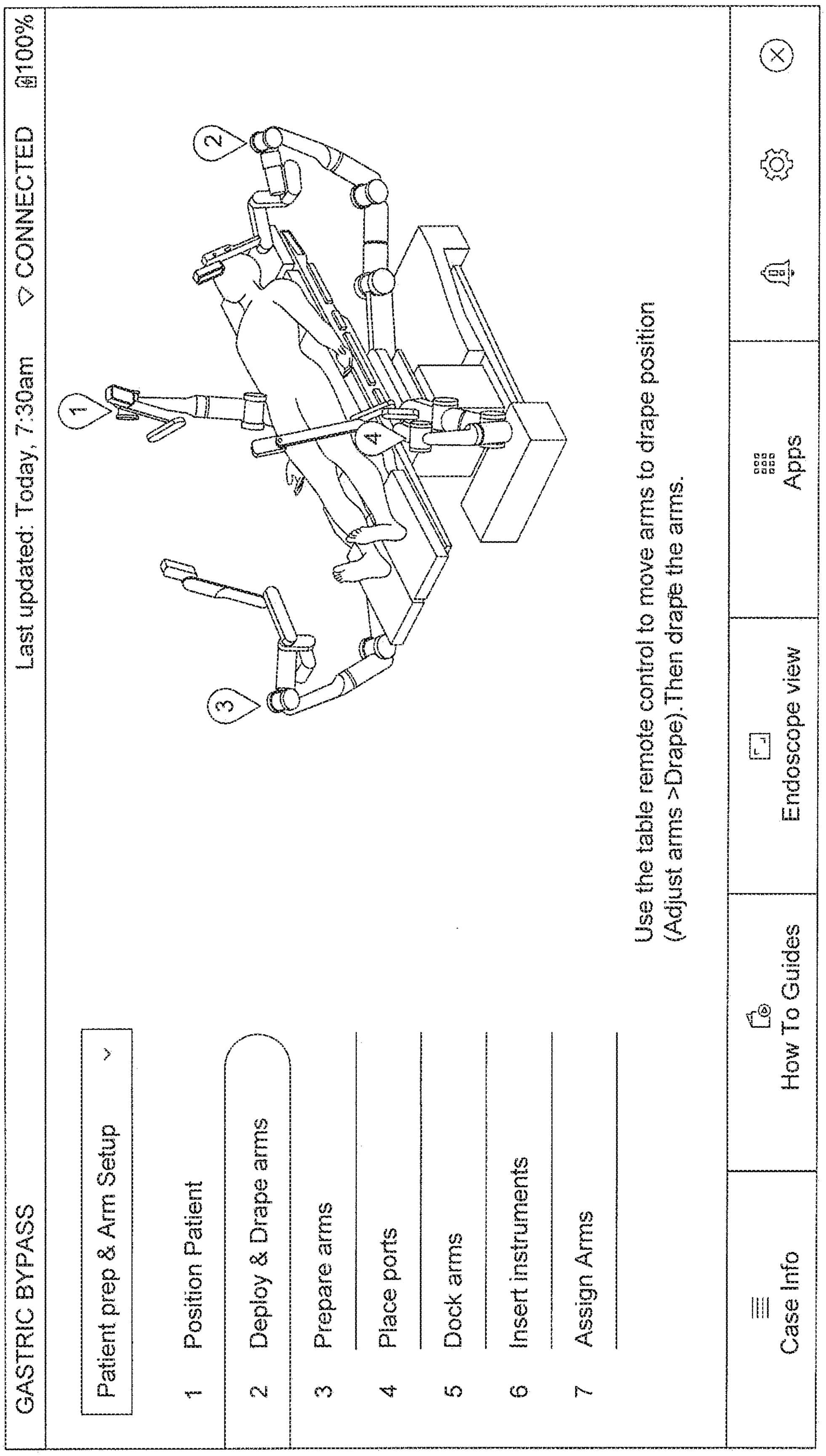
FIG. 7 is an illustration of a graphical user interface of an embodiment that includes a stadium view application that provides an instruction on how to drape robotic arms.
Figure 8:
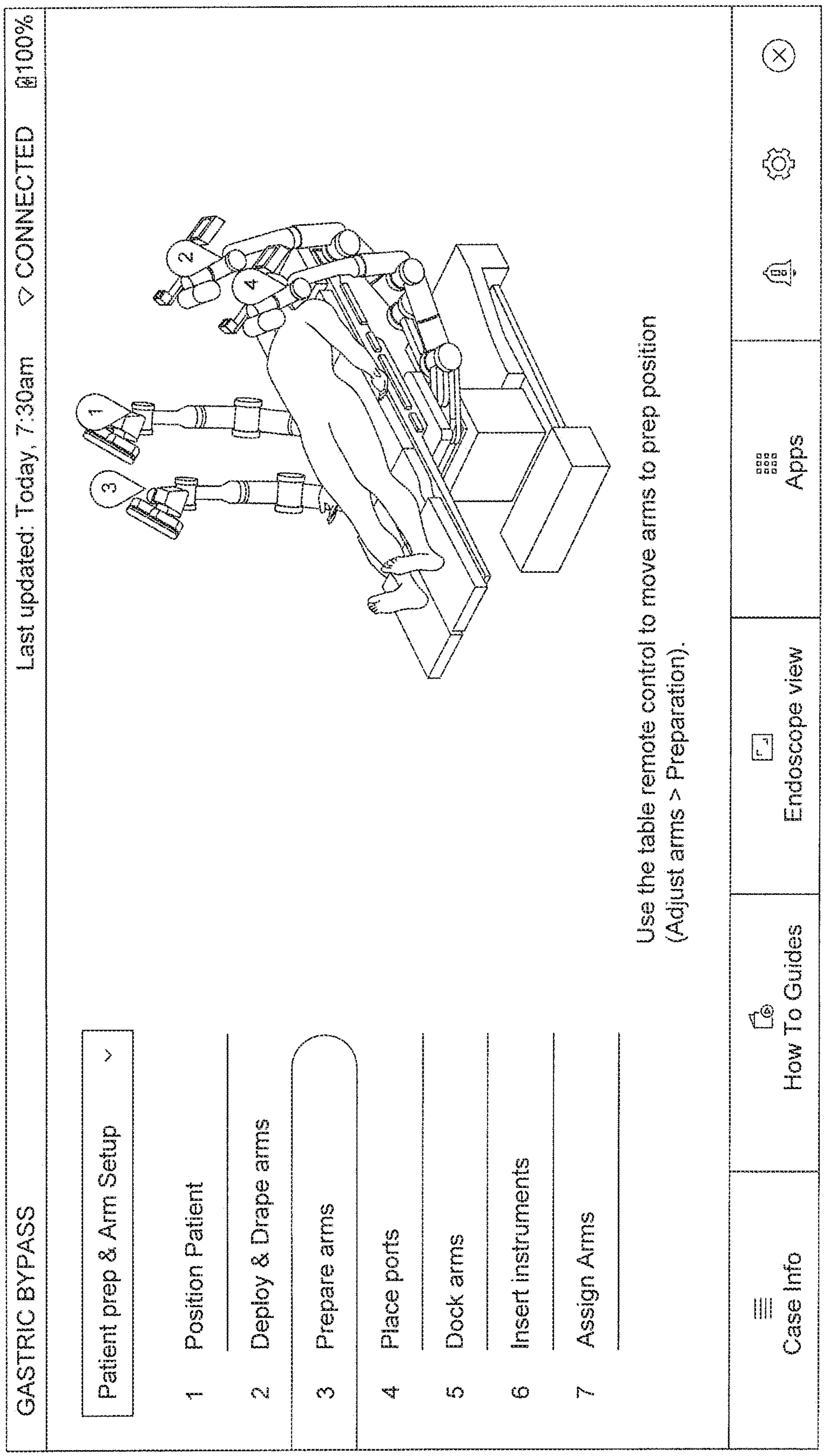
FIG. 8 is an illustration of a graphical user interface of an embodiment that includes a stadium view application that provides an instruction on how to move robotic arms to a prepare arms position.
Figure 9:
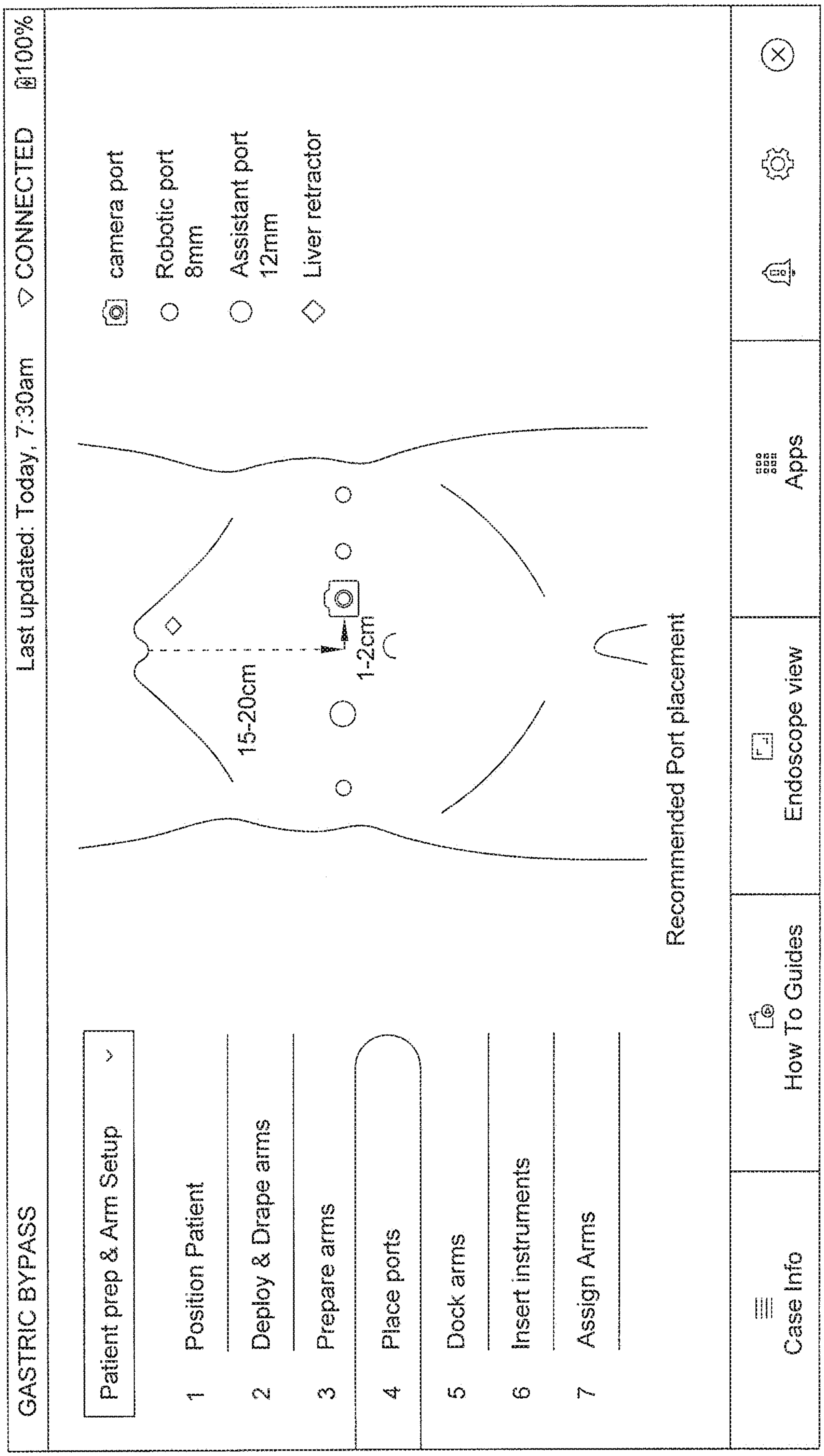
FIG. 9 is an illustration of a graphical user interface of an embodiment that includes a stadium view application that provides an instruction on how to place ports in a patient.
Figure 10:
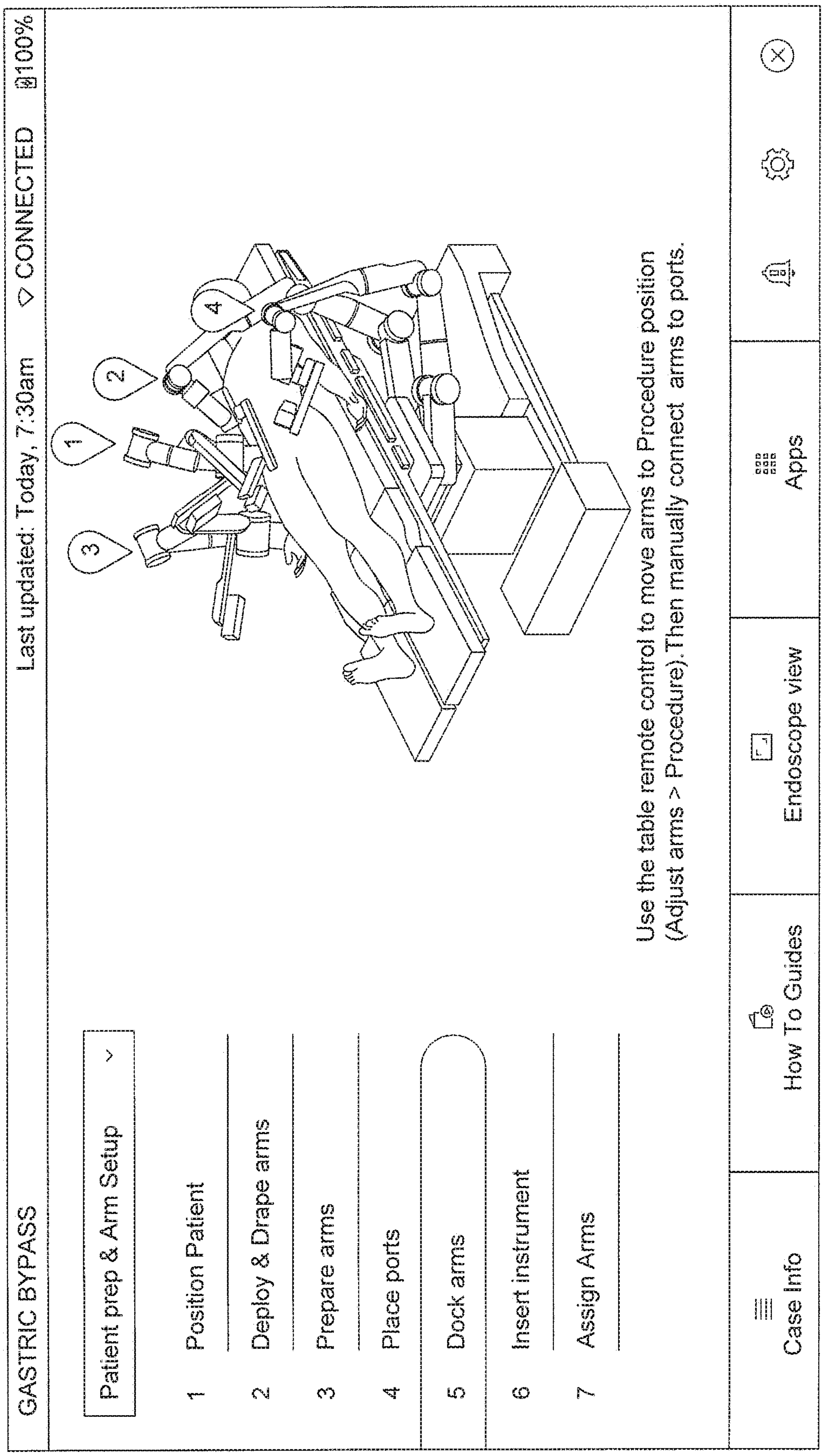
FIG. 10 is an illustration of a graphical user interface of an embodiment that includes a stadium view application that provides an instruction on how to deploy robotic arms to a dock arms position.
Figure 11:
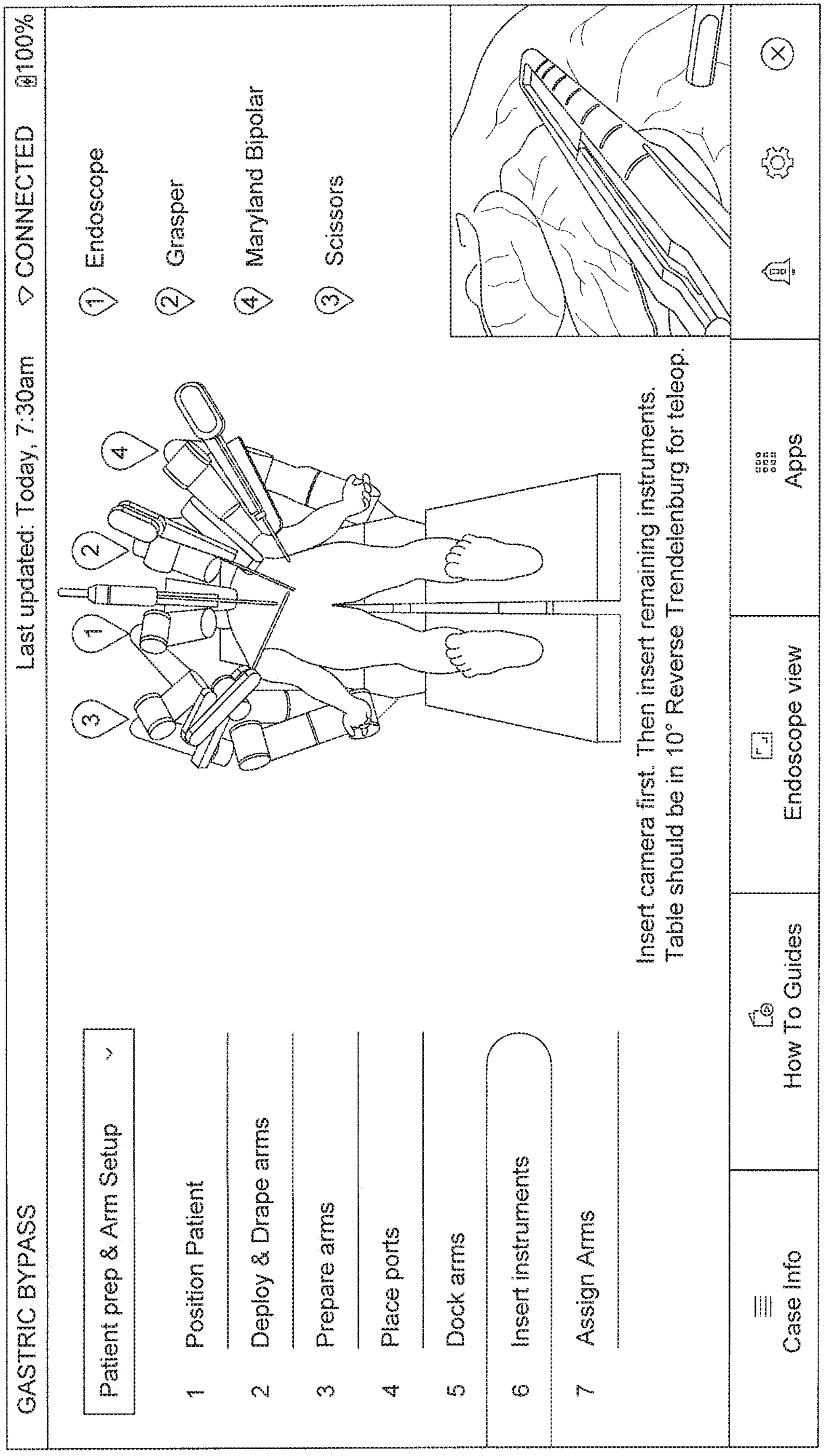
FIG. 11 is an illustration of a graphical user interface of an embodiment that includes a stadium view application that provides an instruction on how to insert instruments in robotic arms.
Figure 12:
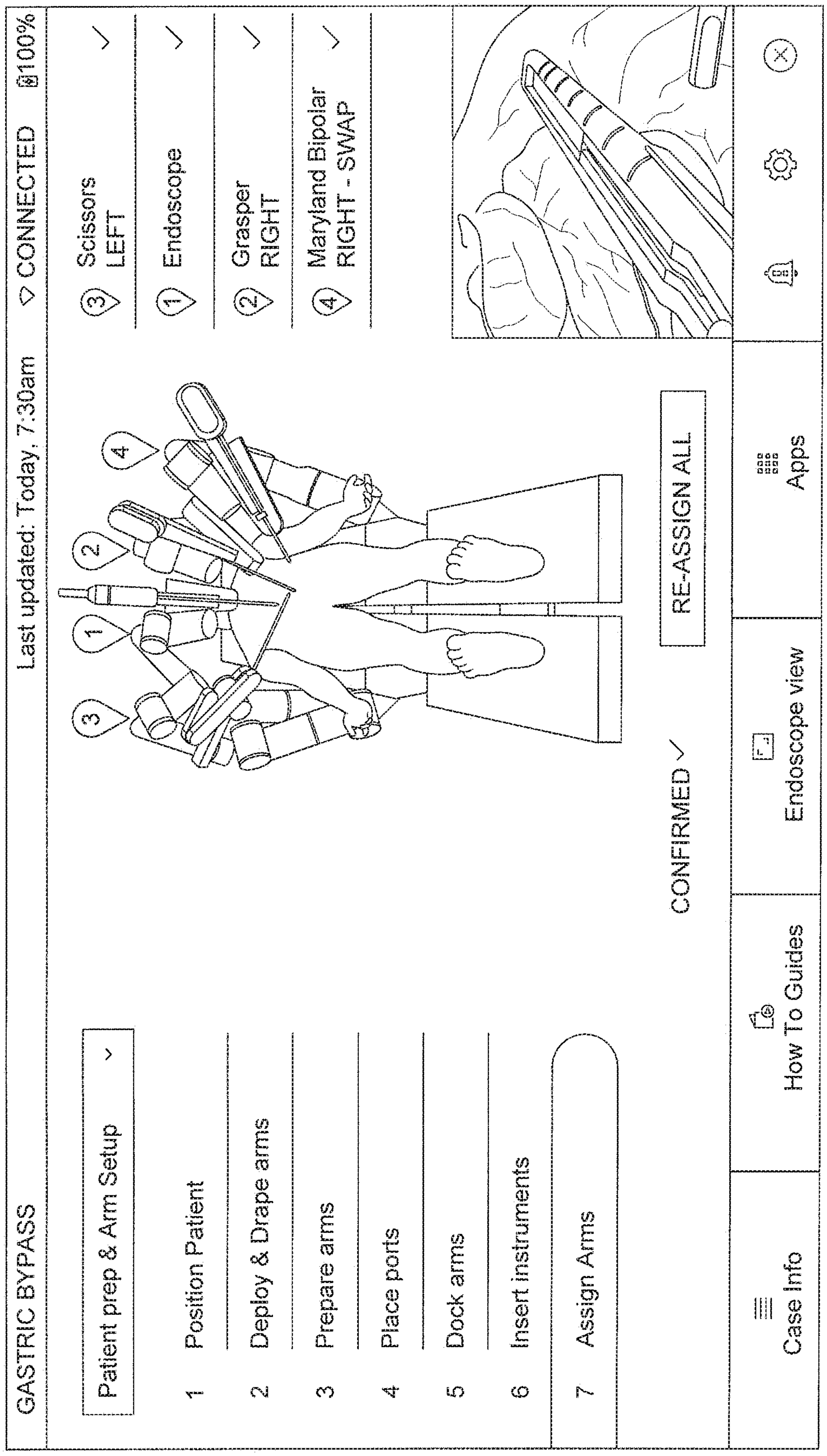
FIG. 12 is an illustration of a graphical user interface of an embodiment that includes a stadium view application that provides an instruction on how to deploy robotic arms to an assign arms position.

FIG. 5 is an illustration of a graphical user interface of an embodiment that includes a stadium view application that provides user-guidance information on how to position a patient. FIG. 6 is an illustration of a graphical user interface of an embodiment that includes a stadium view application that provides user-guidance information on how to deploy robotic arms. Movement of the arms can be done, for example, using a user input device (e.g., remote control). FIG. 7 is an illustration of a graphical user interface of an embodiment that includes a stadium view application that provides an instruction on how to drape robotic arms. FIG. 8 is an illustration of a graphical user interface of an embodiment that includes a stadium view application that provides an instruction on how to move robotic arms to a prepare arms position. FIG. 9 is an illustration of a graphical user interface of an embodiment that includes a stadium view application that provides an instruction on how to place ports in a patient. FIG. 10 is an illustration of a graphical user interface of an embodiment that includes a stadium view application that provides an instruction on how to deploy robotic arms to a dock arms position. FIG. 11 is an illustration of a graphical user interface of an embodiment that includes a stadium view application that provides an instruction on how to insert instruments in robotic arms. FIG. 12 is an illustration of a graphical user interface of an embodiment that includes a stadium view application that provides an instruction on how to deploy robotic arms to an assign arms position.

In one embodiment, the rendered display of one or more portions of the robotic system can be modified to help guide a surgical team during setup and/or teardown (e.g., pre-operative and/or post-operative procedures) of the robotic surgical system 150, or otherwise tend to the system 150. That is, in addition to displaying a graphical representation of current positions of the table and plurality of robotic arms 160, the GUI can display user-guidance information on how to move the plurality of robotic arms 160 to a different position (e.g., an arm setup position or an arm teardown position). This embodiment will now be discussed in conjunction with FIGS. 13-15.

Figure 13:
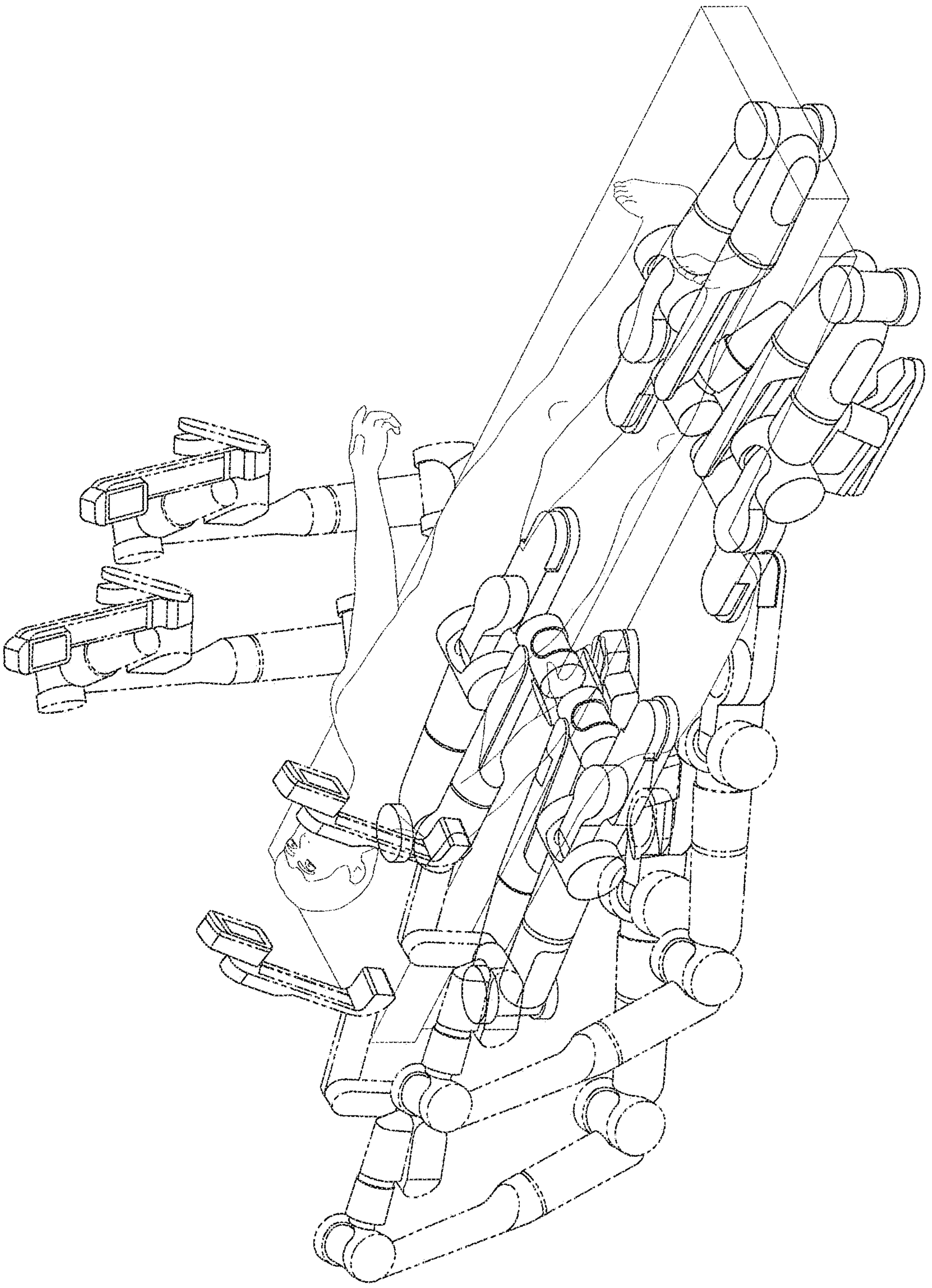
FIG. 13 is an illustration of a graphical user interface of an embodiment that includes a stadium view application that displays user-guidance information on how to move a plurality of robotic arms to an arm setup position.

FIG. 13 shows a graphical representation of current positions of the table and plurality of robotic arms 160. The arms 160 are in a "stowed away" position under the table. FIG. 13 also shows user-guidance information on how to move the plurality of robotic arms 160 to a different position (here, a fully-deployed position). The user guidance information in this example is the display of graphical representation of the plurality of robotic arms in that different position. As shown in FIG. 13, the graphical representation of the current position of the plurality of robotic arms 160 is in solid line, and the graphical representation of the plurality of robotic arms 160 in the different position is in phantom line. However, other ways of displaying and conveying this user-guidance information can be used.

Figure 14:
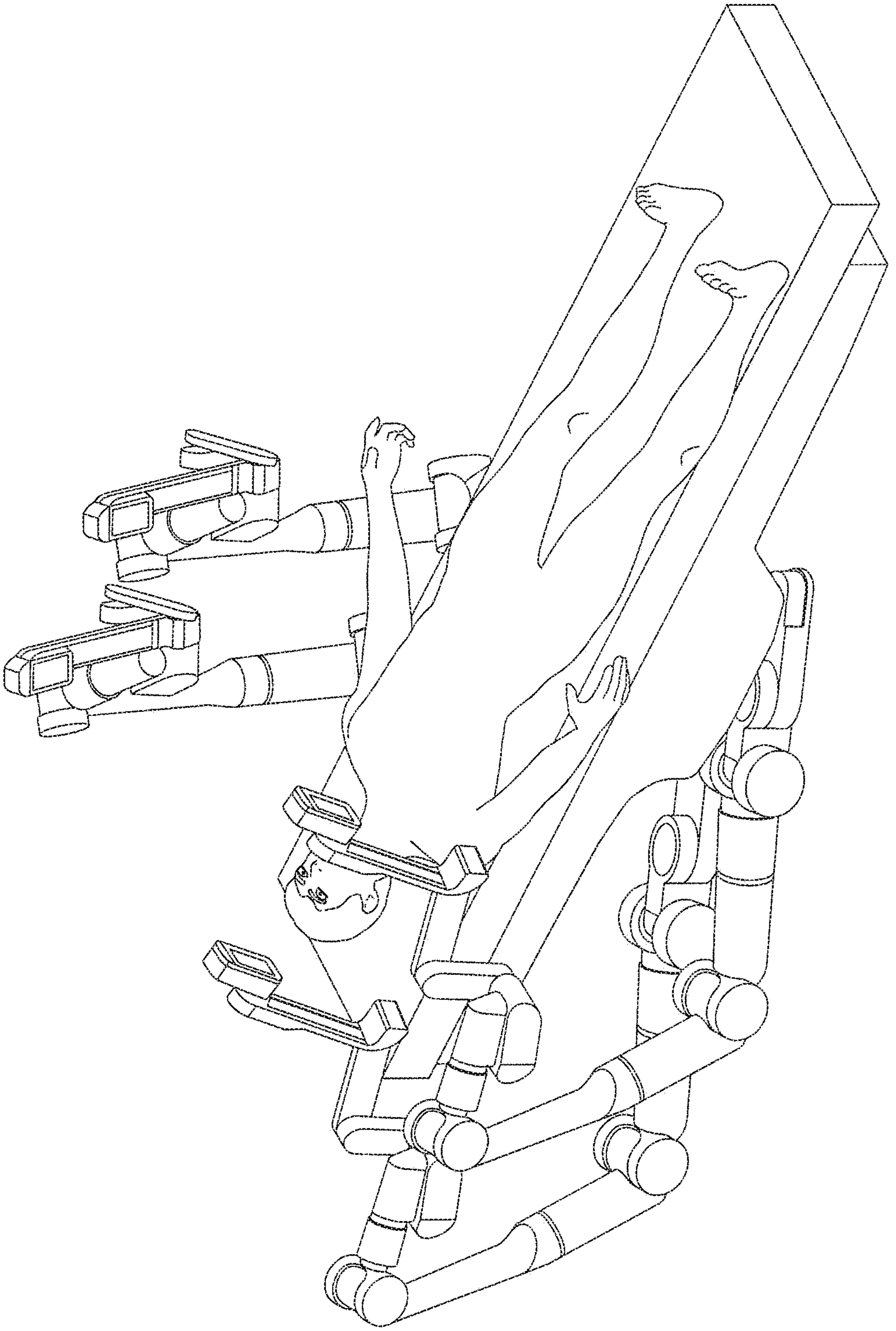
FIG. 14 is an illustration of a graphical user interface of an embodiment that includes a stadium view application that displays a plurality of robotic arms in a deployed position.

By being able to see where the arms 160 should be positioned to, the user can simply move the arms 160 until the graphical representation of the current position of the robotic arm 160 overlaps the graphical representation of the "destination position" of the robotic arm 160 (see FIG. 14). Because the graphical representation of the current position of the robotic arm 160 moves as the user is moving the arm, the user is getting continuous visual feedback on what do to to position the robotic arm 160 in place. Optionally, the robotic surgical system 150 can provide audible user-guidance information on how to move the plurality of robotic arms 160 to the different position. For example, as the user is moving the robotic arm 160 closer to its intended position, the system 150 can provide an auditory cue, such as a sound that "beeps" more when the user is on the right track, followed by a different sound to indicate successful positioning.

Figure 15:
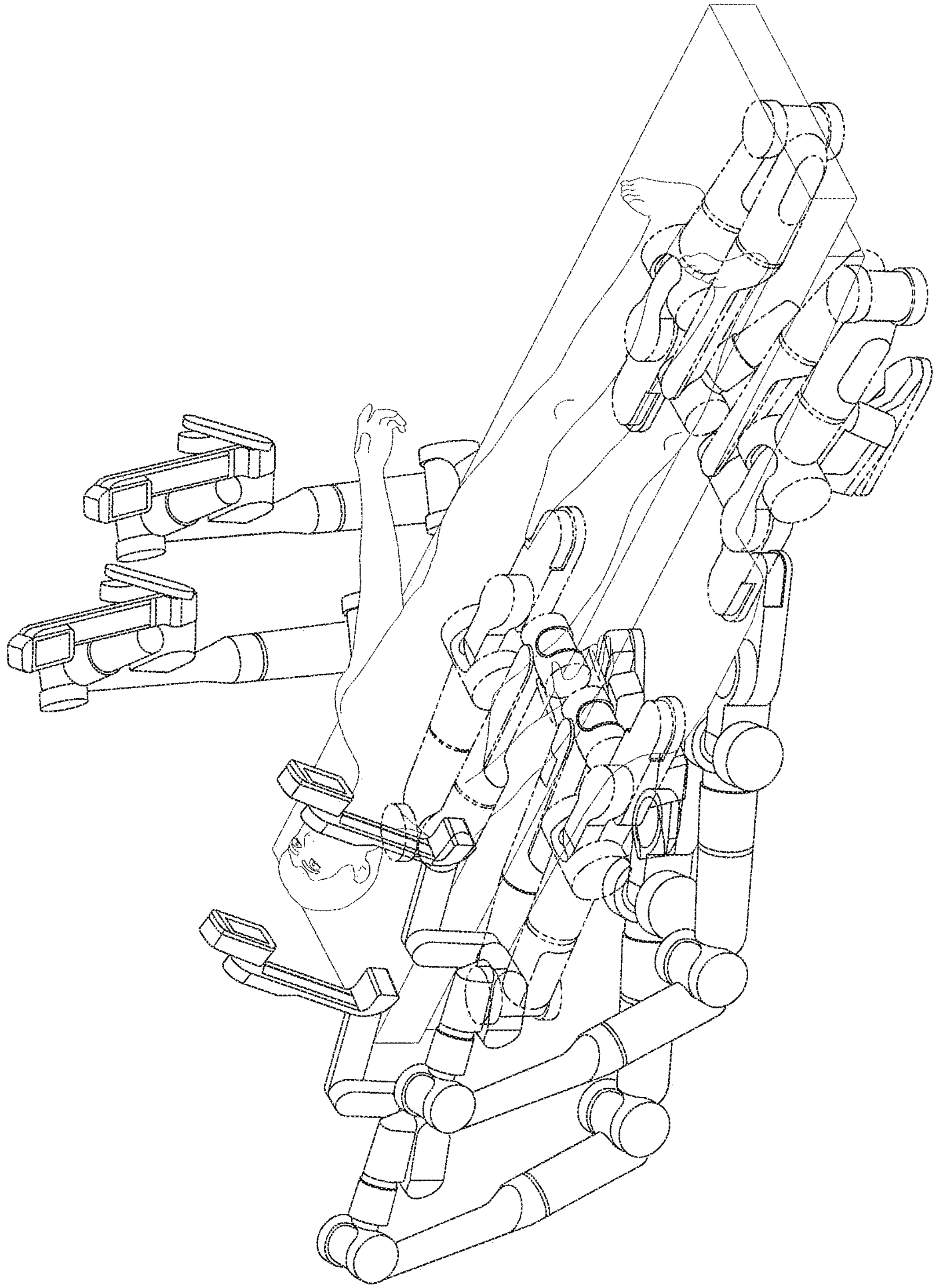
FIG. 15 is an illustration of a graphical user interface of an embodiment that includes a stadium view application that displays user-guidance information on how to move a plurality of robotic arms to a stowed position.

While FIG. 13 shows an example of an arm-setup situation, FIG. 15 shows how a GUI with a stadium view can be used in an arm-tear-down situation to stow the robotic arm 160. As shown in FIG. 15, the arms in the stowed-away position are shown in phantom, and a user would move the robotic arms 160 to the positions shown in phantom to stow away the arms 160.

Figure 16:
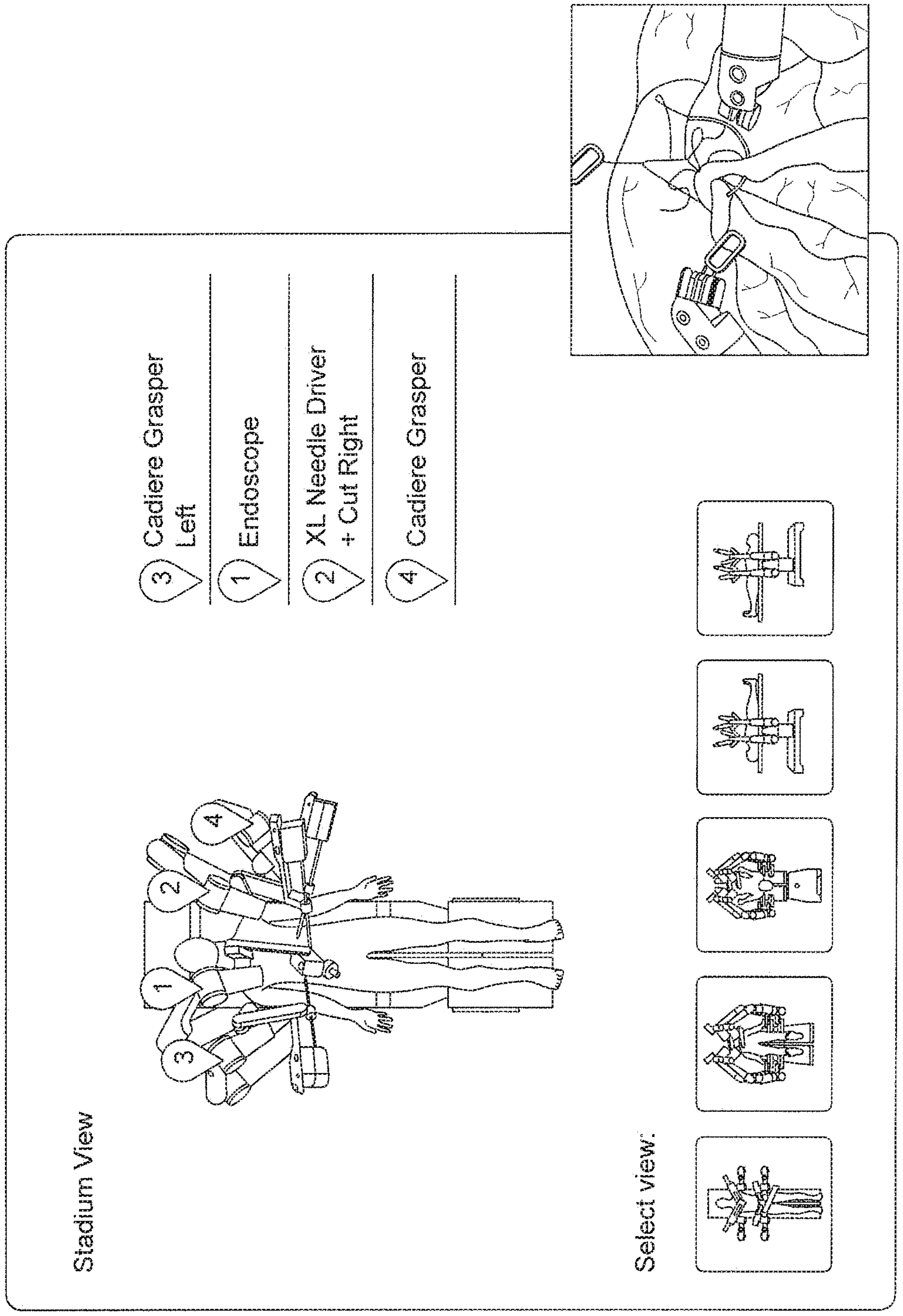
FIG. 16 is an illustration of a graphical user interface of another embodiment.

Of course, these are merely examples, and other implementations of user-guidance information can be used. For example, instead of just indicating the final position of a robotic arm 160 with a static image, the GUI can provide an animation/video showing exactly how the robotic arm 160 should be manipulated to move it to its final position. As another example, the user-guidance information can be a display of what touchpoints on the robotic arms 160 to press and how to move the robotic arms 160. As yet another example, in addition to a graphical representation of the arm 160, table, and patient, the stadium view can also include an endoscopic view of the surgical site (captured by an endoscopic camera on one of the robotic arms 160). Further, these embodiments can be used to guide the user in patient and table accessory positioning. This can help enable the stadium view to reflect the precise position of the patent on the table. Additionally, these embodiments can be used to automatically detect when a user has skipped or missed a setup/teardown step and inform the user of this with guidance on how to resolve the issue. Finally, as noted above, the images shown in the drawings are just examples, and other graphics or representations can be used. For example, FIG. 16 is an illustration of a graphical user interface of another embodiment.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

What is claimed is:

1. A robotic surgical system comprising:

a plurality of robotic arms;

a display device; and a processor configured to:

render, on the display device, a graphical representation of a model module of the plurality of robotic arms in a current position, a kinematic model of the robotic arms input to the model module to render the graphical representation, wherein the graphical representation moves to reflect position change of the plurality of robotic arms in real-time based on the kinematic model.

2. The robotic surgical system of claim 1, wherein the processor is configured to display, on the display device, user-guidance information on how to move the plurality of robotic arms to a different position, wherein the different position is a deployed position.

3. The robotic surgical system of claim 1, wherein the processor is configured to display, on the display device, user-guidance information on how to move the plurality of robotic arms to a different position, wherein the different position is a stowed position.

4. The robotic surgical system of claim 1, wherein the processor is configured to display, on the display device, user-guidance information on how to move the plurality of robotic arms to a different position, wherein the graphical representation of the plurality of robotic arms in the current position is in solid line, and wherein the user-guidance information comprises a graphical representation in phantom line of the plurality of robotic arms in the different position.

5. The robotic surgical system of claim 1, wherein the processor is configured to display, on the display device, user-guidance information on how to move the plurality of robotic arms to a different position, wherein the user-guidance information comprises an instruction on how to manipulate a user input device to move the plurality of robotic arms to the different position.

6. The robotic surgical system of claim 1, wherein the processor is further configured to provide audible user-guidance information.

7. The robotic surgical system of claim 1, wherein the display device is located adjacent to a patient table.

8. The robotic surgical system of claim 1, wherein the processor is configured to display, on the display device, user-guidance information on how to move the plurality of robotic arms to a different position, wherein the user-guidance information comprises an indication of which touchpoints on the plurality of robotic arms to manipulate.

9. A method for a robotic surgical system, the method comprising:

performing rendering and displaying in a static image in a robotic surgical system comprising a plurality of robotic arms and a display device:

wherein the rendering comprises rendering, on the display device, a graphical representation of current positions of the plurality of robotic arms; and wherein the displaying comprises displaying, on the display device, a graphical representation of destination positions of the plurality of robotic arms rendered from a kinematic model of the robotic arms, wherein the graphical representation of the destination positions of the plurality of robotic arms is displayed differently than the graphical representation of the current positions of the plurality of robotic arms;

wherein the graphical representation of the destination positions of the plurality of robotic arms and the graphical representation of the current positions of the plurality of robotic arms each comprises a drawn object different than a camera view.

10. The method of claim 9, wherein the graphical representation of the destination positions of the plurality of robotic arms is displayed in phantom lines, and wherein the graphical representation of the current positions of the plurality of robotic arms is rendered in solid lines.

11. The method of claim 9, wherein the destination position is one of the following: the plurality of robotic arms in deployed positions and stowed positions.

12. The method of claim 9, further comprising providing audible user-guidance information.

13. The method of claim 9, wherein the display device is located adjacent to a patient table.

14. The method of claim 9, further comprising displaying an indication of which touchpoints on the plurality of robotic arms to manipulate.

15. A robotic surgical system comprising:

a plurality of robotic arms; and means for providing user guidance information on how to move the plurality of robotic arms to a different position, wherein the means for providing comprises means for providing instruction on how to manipulate a user input device to move the plurality of robotic arms to the different position, wherein the means for providing comprises means for displaying, on a display device, a graphical representation of the plurality of robotic arms in the different position alongside a rendered display of a graphical representation of the plurality of robotic arms in a current position and based on a kinematic model of the robotic arms.

16. The robotic surgical system of claim 15, wherein the graphical representation of the plurality of robotic arms in the different position is displayed differently than the rendered graphical representation of the plurality of robotic arms in the current position.

17. The robotic surgical system of claim 15, wherein the means for providing comprises means for providing audible user-guidance information.

18. The robotic surgical system of claim 15, wherein the display device is located adjacent to a patient table.

* * * * *